(12) United States Patent
Hagihara et al.

(10) Patent No.: US 10,675,262 B2
(45) Date of Patent: Jun. 9, 2020

(54) DEVELOPMENT OF DIETARY THERAPY IN CANCER

(71) Applicants: Osaka University, Osaka (JP); Meiji Co., Ltd., Tokyo (JP)

(72) Inventors: Keisuke Hagihara, Osaka (JP); Kinya Ashida, Kanagawa (JP); Hidekazu Tonouchi, Kanagawa (JP); Kentaro Nakamura, Kanagawa (JP)

(73) Assignees: OSAKA UNIVERSITY, Osaka (JP); Meiji Co., Ltd., Tokyo (JP)

( * ) Notice: Subject to any disclaimer, the term of this patent is extended or adjusted under 35 U.S.C. 154(b) by 0 days.

(21) Appl. No.: 15/747,800

(22) PCT Filed: Sep. 2, 2016

(86) PCT No.: PCT/JP2016/004023
§ 371 (c)(1),
(2) Date: Jan. 26, 2018

(87) PCT Pub. No.: WO2017/038101
PCT Pub. Date: Mar. 9, 2017

(65) Prior Publication Data
US 2018/0214410 A1 Aug. 2, 2018

(30) Foreign Application Priority Data
Sep. 4, 2015 (JP) ................................ 2015-175198

(51) Int. Cl.
| | |
|---|---|
| *A61K 31/225* | (2006.01) |
| *A61K 31/7016* | (2006.01) |
| *A23L 33/00* | (2016.01) |
| *A23L 33/115* | (2016.01) |
| *A61P 35/00* | (2006.01) |
| *A61K 45/06* | (2006.01) |
| *A61K 31/22* | (2006.01) |
| *A61K 45/00* | (2006.01) |
| *A61K 33/30* | (2006.01) |

(52) U.S. Cl.
CPC .......... *A61K 31/225* (2013.01); *A23L 33/115* (2016.08); *A23L 33/30* (2016.08); *A61K 31/22* (2013.01); *A61K 31/7016* (2013.01); *A61K 45/00* (2013.01); *A61P 35/00* (2018.01); *A23V 2002/00* (2013.01)

(58) Field of Classification Search
CPC .. A61K 31/225; A61K 31/00; A61K 31/7016; A23L 33/30; A23L 33/115; A61P 35/00; A23V 2002/00; A23V 2200/308; A23V 2200/332; A23V 2200/3322
See application file for complete search history.

(56) References Cited

U.S. PATENT DOCUMENTS

2008/0089981 A1* 4/2008 Butler ................ A23L 2/39 426/72
2013/0157937 A1* 6/2013 Lynch ................ A61K 31/20 514/5.7
2014/0011749 A1* 1/2014 Lynch ................ A61K 31/202 514/19.3
2014/0072654 A1* 3/2014 D'Agostino .......... A61K 45/06 424/613

FOREIGN PATENT DOCUMENTS

| WO | WO-2012/113415 A1 | 8/2012 |
| WO | WO-2014/085652 A1 | 6/2014 |
| WO | WO-2014/159500 A1 | 10/2014 |

OTHER PUBLICATIONS

Fearon et. al., American Journal of Clinical Nutrition, 1988, American Society for Clinical Nutrition, vol. 47, pp. 42-48 (Year: 1988).*
USDA, United States Department of Agriculture, National Agriculture Library, "How many calories are in one gram of fat, carbohydrate, or protein?", publication date not provided, accessed online on Oct. 3, 2018 at: https://www.nal.usda.gov/fnic/how-many-calories-are-one-gram-fat-carbohydrate-or-protein (Year: 2018).*
Rieger et. al., Int. J. Oncology, 2014, vol. 44, pp. 1843-1852 (Year: 2014).*
Arends et. al., Clinical Nutrition, 2017, vol. 36, pp. 11-48 (Year: 2017).*
International Application No. PCT/JP2016/004023, International Search Report (English Translation), dated Sep. 27, 2016.
Otto et al., Growth of human gastric cancer cells in nude mice is delayed by a ketogenic diet supplemented with omega-3 fatty acids and medium-chain triglycerides, BMC Cancer, 8:122 (2008).
Zhou et al., The calorically restricted ketogenic diet, an effective alternative therapy for malignant brain cancer, Nutr. Metab (Lond.), 4:5 (2007).
Zuccoli et al., Metabolic management of glioblastoma multiforme using standard therapy together with a restricted ketogenic diet: Case Report, Nutr. Metab. (Lond.), 7:33 (2010).
Hao et al., Growth of human colon cancer cells in nude mice is delayed by ketogenic diet with or without omega-3 fatty acids and medium-chain triglycerides, Asian Pac. J. Cancer Prev., 16(5):2061-8 (2015).
Singapore Patent Application No. 11201800657V, Search Report, dated Apr. 8, 2019.
Singapore Patent Application No. 11201800657V, Written Opinion, dated Apr. 8, 2019.

* cited by examiner

*Primary Examiner* — Sarah Pihonak
(74) *Attorney, Agent, or Firm* — Marshall, Gerstein & Borun LLP

(57) ABSTRACT

The invention provides new compositions or combinations thereof for the treatment of cancer. More specifically, the invention provides compositions or combinations thereof for cancer treatment including a high-fat diet. Specifically, the high-fat diet is characterized by having approximately 120 g/day or more, or approximately 70% or more of the total daily energy, from fat, based on a real body weight of 50 kg. The diet is preferably a carbohydrate-restricted high-fat diet, and more preferably provided by a ketone formula and/or MCT oil. The dietary therapy by a high-fat diet of the present invention is provided along with surgical treatment, chemotherapy or radiation therapy, or combinations thereof.

5 Claims, 19 Drawing Sheets

Fig.9
Blood data for 3 cases with continued ketogenic diet
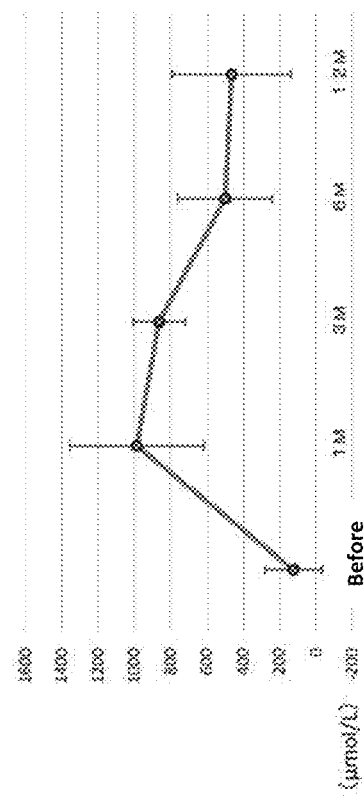
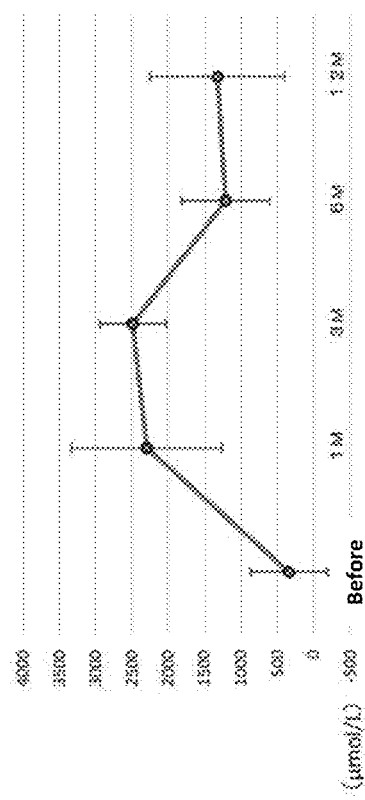

Fig.10 Blood data for 3 cases with continued ketogenic diet

Fig.13
• Change in CT of case 8
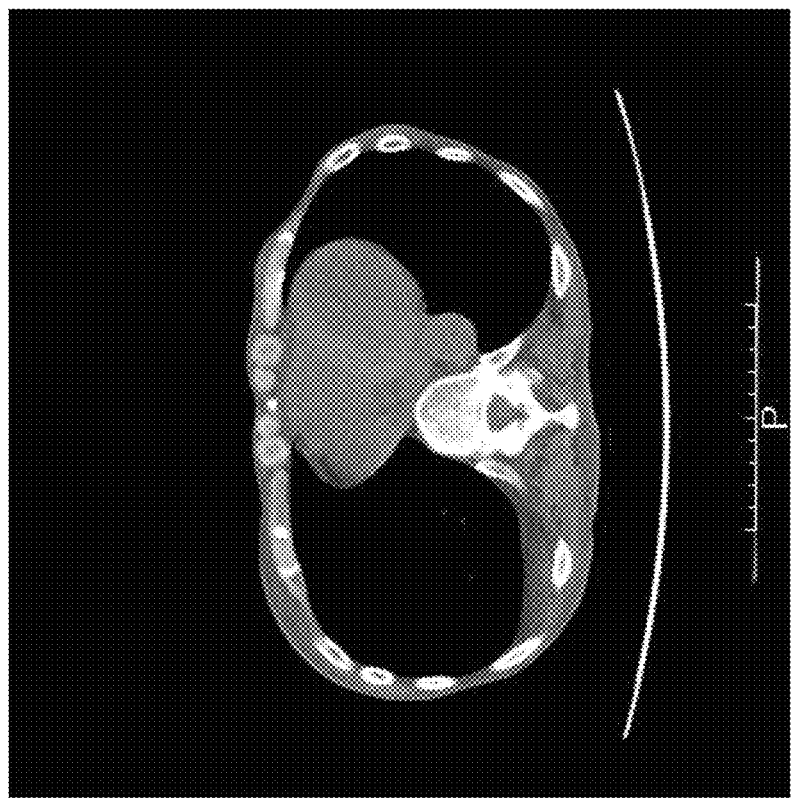
November 25, 2015
August 31, 2015

Fig.14
• Change in PET-CT of case 11
October 2, 2015
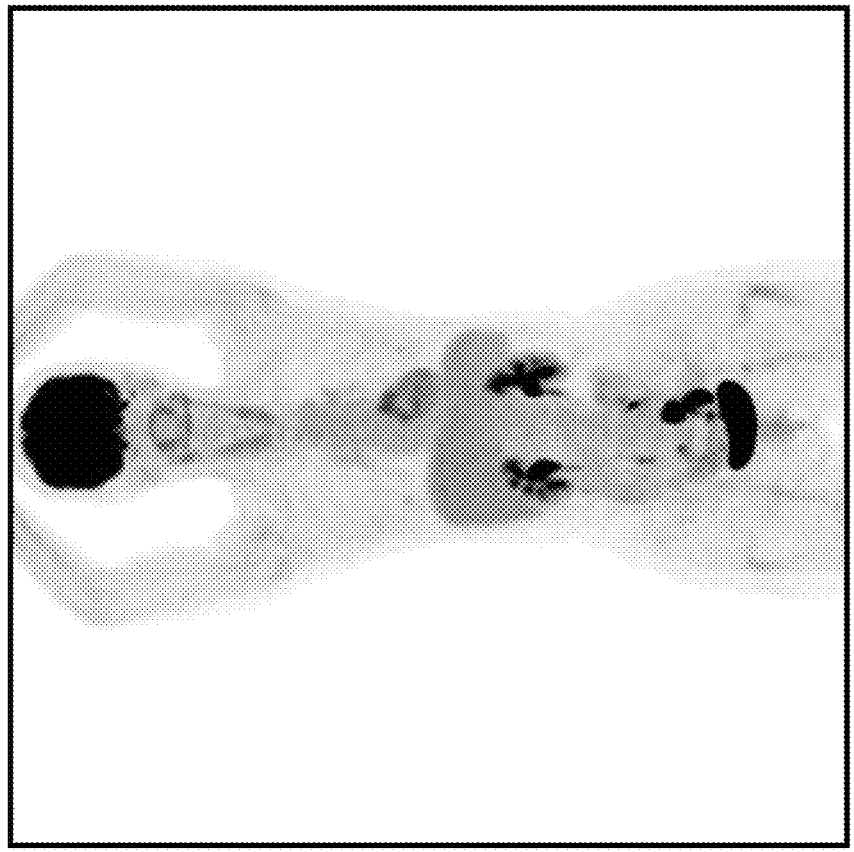
February 4, 2016

Fig.15 Change in PET-CT of case 11
February 4, 2016
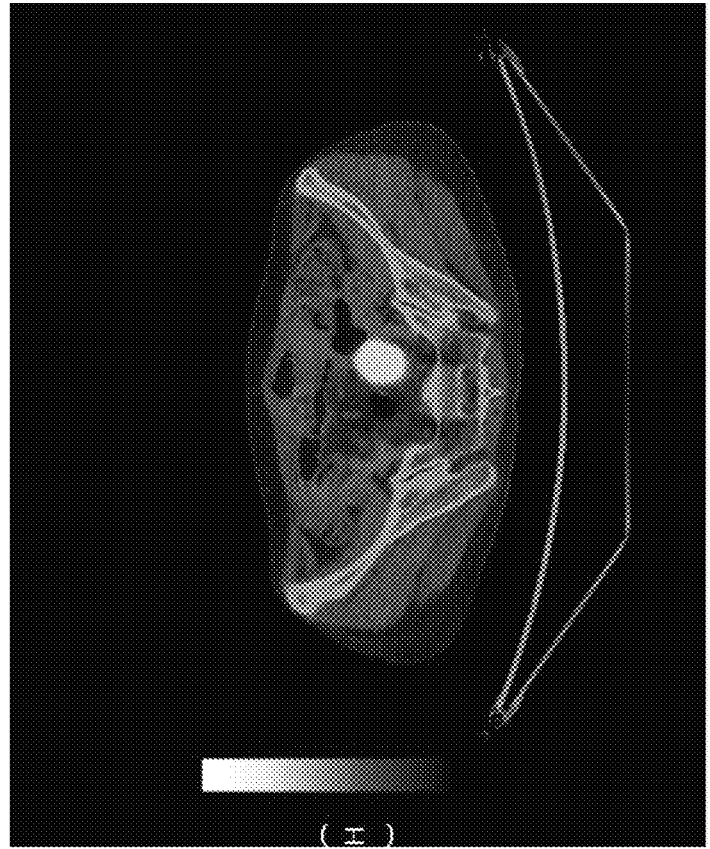
October 2, 2015

Fig.16
- Change in PET-CT of case 11
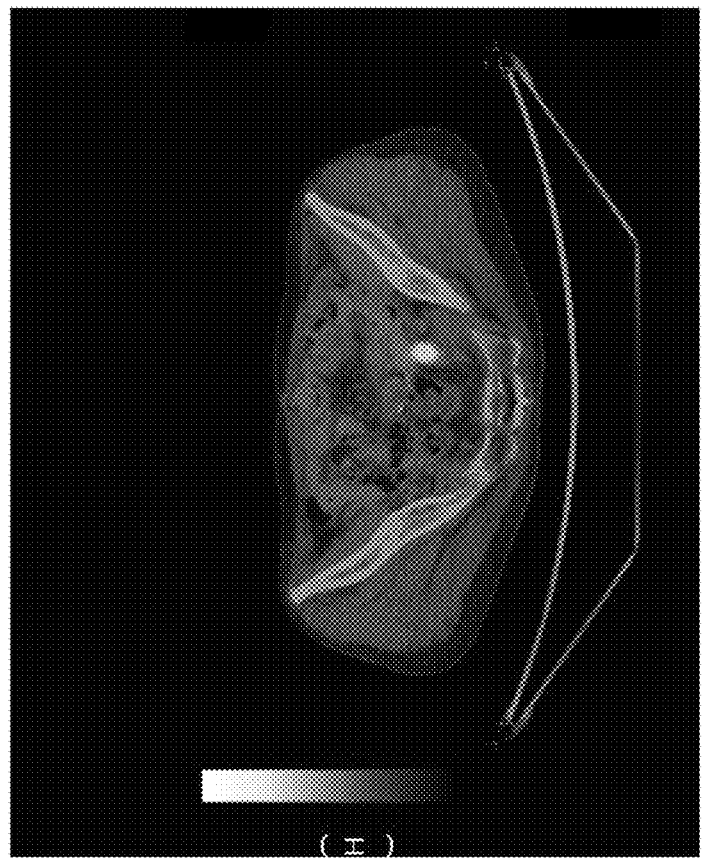
February 4, 2016
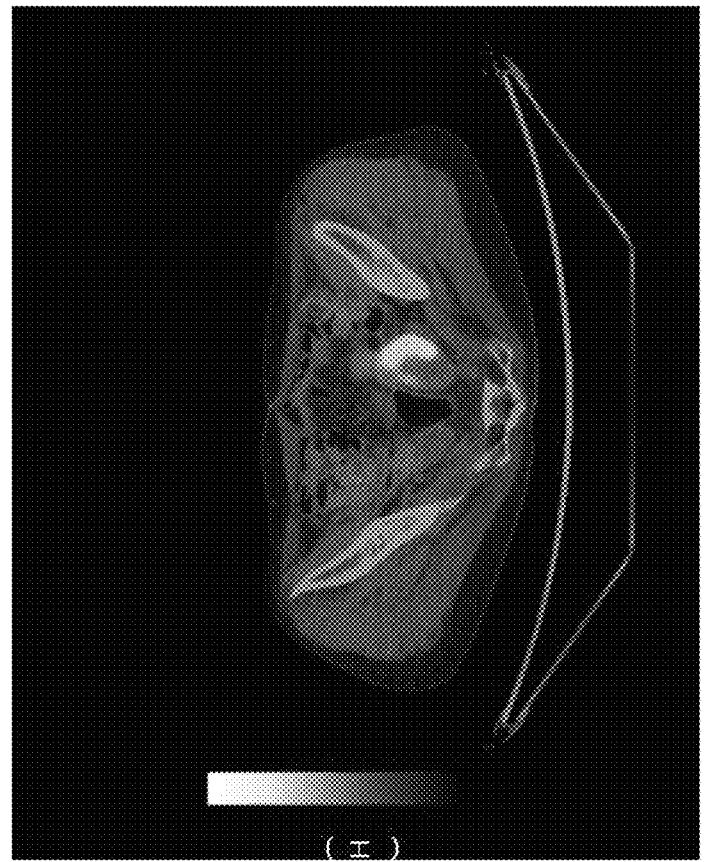
October 2, 2015

Fig.17
- Change in PET-CT of case 12
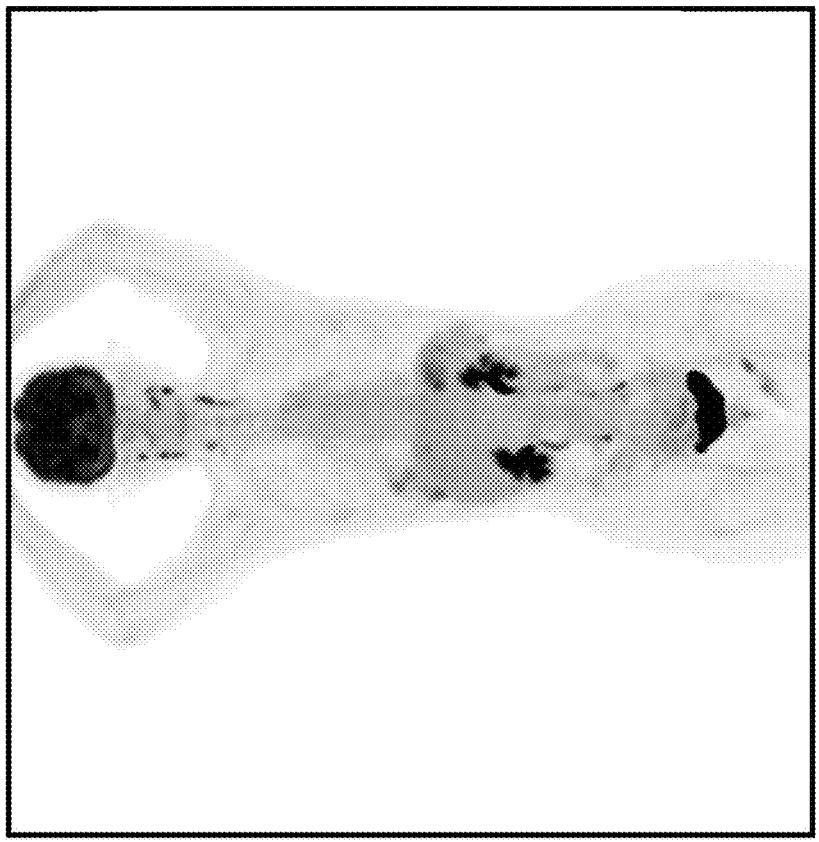
February 10, 2016
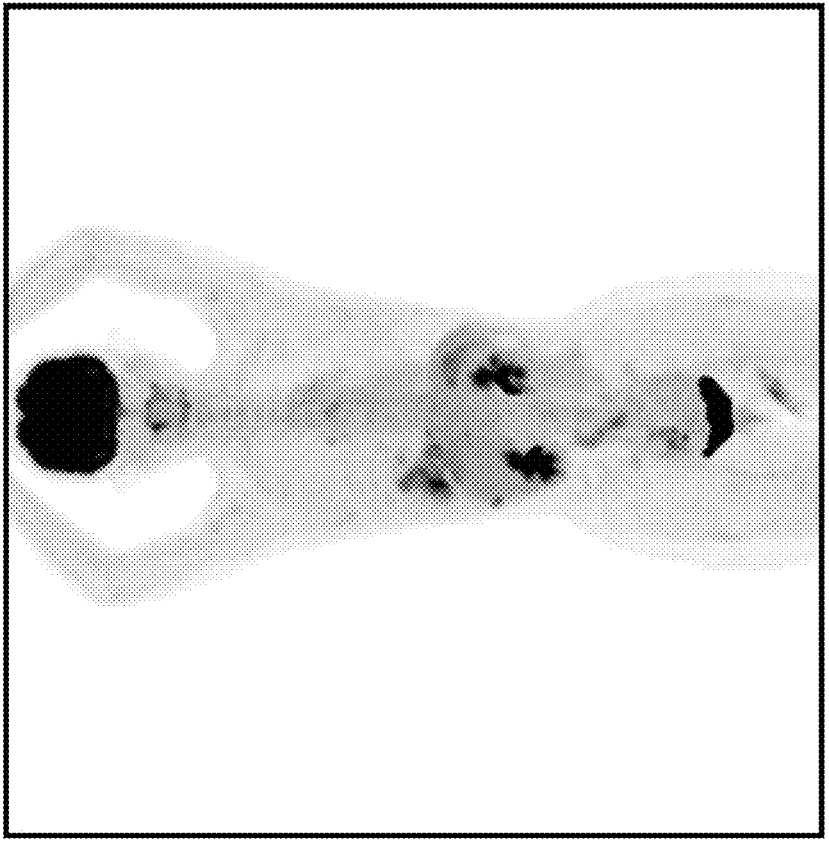
November 18, 2015

Fig.18
Change in PET-CT of case 12
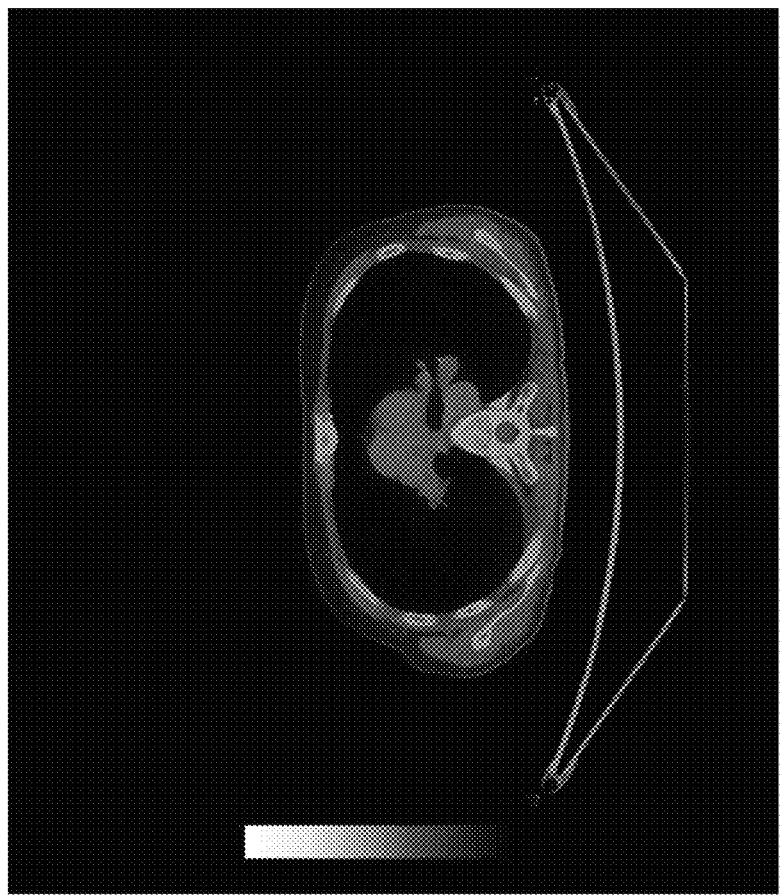
November 18, 2015
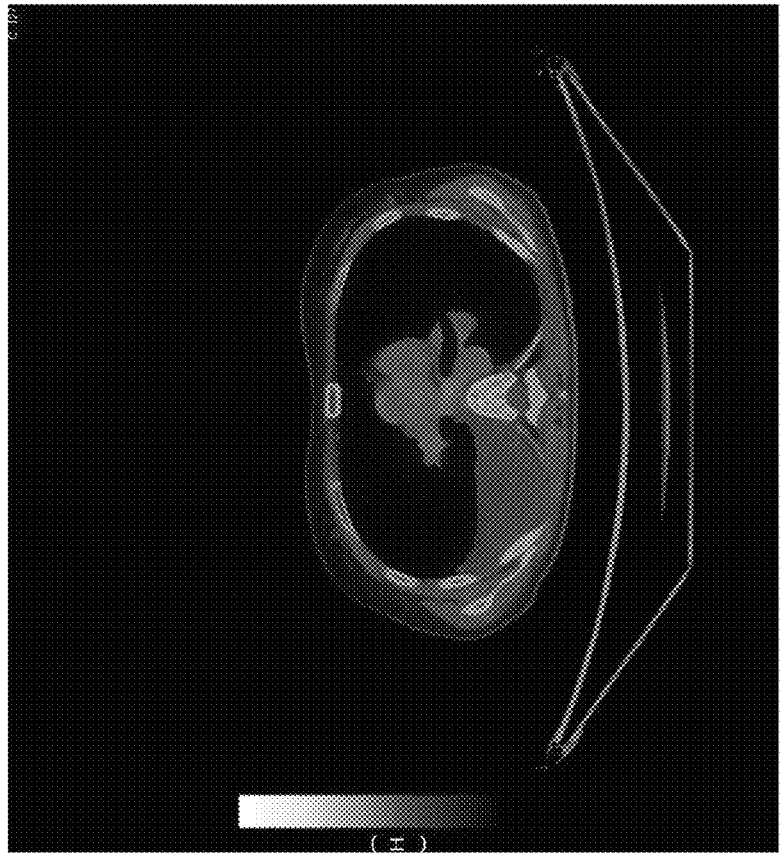
February 10, 2016

Fig.19
Change in PET-CT of case 12
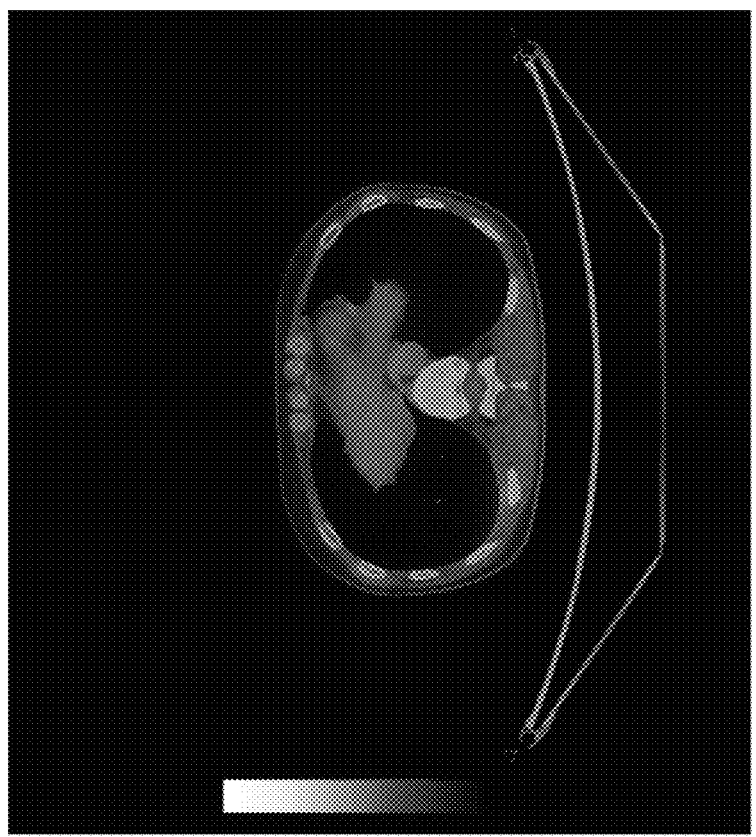
February 10, 2016
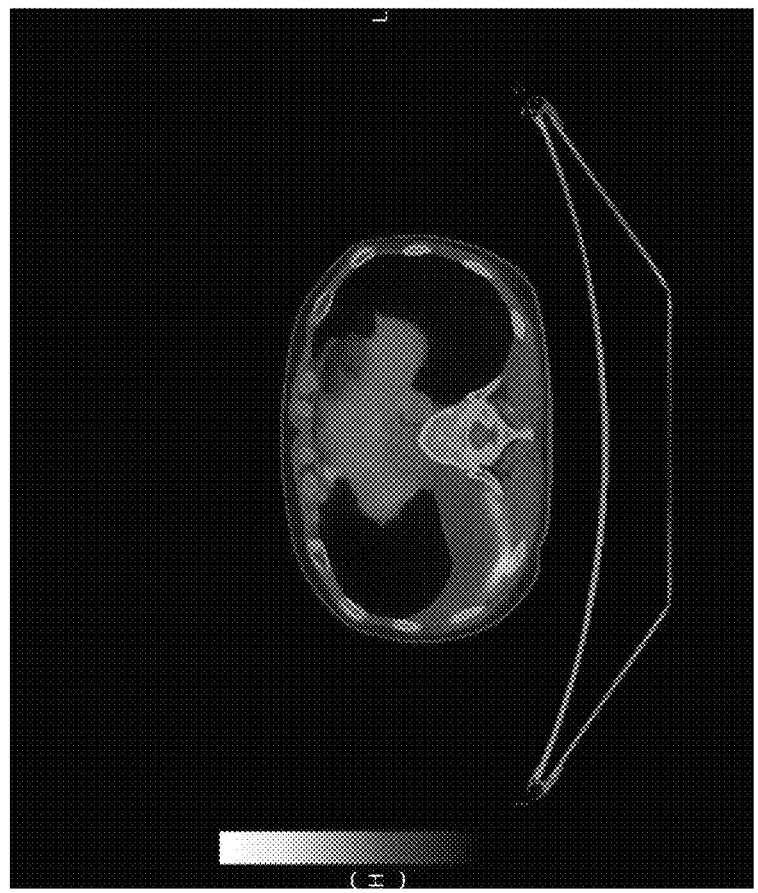
November 18, 2015

DEVELOPMENT OF DIETARY THERAPY IN CANCER

TECHNICAL FIELD

The present invention relates to a technical field associated with a composition or a combination for preventing or treating cancer. More specifically, the present invention relates to a composition or a combination for providing dietary therapy in cancer therapy. Even more specifically, the present invention relates to applications of high fat diet, such as available carbohydrate restricted high fat diet, in therapy of terminal cancer.

BACKGROUND ART

In recent years, life prognosis of patients has significantly improved for carcinoma such as gastric cancer or colon cancer that can be discovered early and resected. However, pancreatic cancer, gallbladder cancer, lung cancer and the like are often discovered as advanced cancer. In addition, chemotherapy and radiation therapy, which have significant side effects and impair QOL, are concurrently used in some cases such that the prognosis is not considered as clearly improved (National Cancer Center Japan, Monitoring of Cancer Incidence in Japan—Survival 2000-2002 report).

With westernization of diet in recent years, cancer found frequently in the West, such as colon cancer, breast cancer, lung cancer, and prostate cancer, is increasing instead of gastric cancer. The follow-up study of about 40,000 males and females between 40 to 69 years of age in 9 regions from year 1990 to 2003 by the research team of the Ministry of Health, Labour and Welfare has reported a result showing that males with a high C peptide value is as much as 3-times more likely to suffer from colon cancer than males with a low value. (Non-Patent Literature 1=Int J Cancer. 2007 May 1; 120(9): 2007-12).

CITATION LIST

Non Patent Literature

[NPL 1] Int J Cancer. 2007 May 1; 120(9): 2007-12

SUMMARY OF INVENTION

Solution to Problem

As a result of diligent research, the inventors conjectured that high fat diet, especially available carbohydrate restricted high fat diet (e.g., so-called "ketogenic diet"), can be one of the therapeutic methods for terminal cancer patients, and examined the usefulness of high fat diet represented by ketogenic diet for Japanese terminal lung cancer patients to discover that a composition or a combination thereof for treating cancer, comprising high fat diet, such as available carbohydrate restricted high fat diet, or preferably a combination of fat at 120 g or greater and/or carbohydrate restricted to 30 g or less per day and/or daily caloric intake of 20 kcal/kg body weight or greater and/or medium chain fatty acid oil (MCT oil) and the like unexpectedly treats cancer and improves quality of life significantly, thereby achieved the present invention.

As one non-limiting test example, the utility of ketogenic formula on cancer was evaluated with a colon-26 cell transplanted cancer bearing mouse model using to confirm the effect of high fiber diet (e.g., available carbohydrate restricted high fat diet). The tumor weight on day 21 after colon-26 cell transplantation was measured, and the result shows a statistically significant decrease in the tumor weight of the ketogenic formula group relative to the control group ($p<0.01$). The carcass weight, which is the body weight minus the tumor weight, was statistically significantly higher in the ketogenic formula group relative to that of the control group. Further, it is commonly known that the energy intake decreases when ketogenic diet (available carbohydrate restricted high fat diet) is given to animals, but there is no difference in the total caloric intake of the ketogenic formula group relative to the control group, thus maintaining the energy intake. The blood ketone body concentration in the ketogenic formula group was significantly higher relative to that of the control group. Furthermore, it was found that the blood inflammatory cytokine (IL-6) concentration was significantly suppressed in the ketogenic formula group relative to the control group. The above results have elucidated that a ketogenic formula effectively increases the blood ketone body concentration, suppresses inflammatory cytokines, and reduces tumor without reducing total energy intake or carcass weight.

A non-limiting test example of a clinical study was started on January 2013, and five informed consents were obtained by March 2015 from two males and three females with an average age of $58.4 \pm 10.1$ years, height of $161.4 \pm 9.7$ cm, body weight of $55.1 \pm 10.4$ kg, and BMI of $20.9 \pm 1.5$. In all cases, the patients had stage IV pulmonary adenocarcinoma. Four patients had a history of chemotherapy and two patients had a history of radiation therapy. One patient withdrew the consent. Ketogenic diet was introduced to 3 patients, but not to one patient due to stomach discomfort. In addition to dietary guidance, MCT oil and ketogenic formula were used. As a result, for blood ketone bodies, acetoacetic acid increased to $986.6 \pm 453.3$ μmol/L and β-H butyrate increased to $2298 \pm 1270.4$ μmol/L in one month. In addition, the expected hypoglycemia, nausea, fatigue or the like was not observed, and improving trend was exhibited in the systemic condition scale from $11.7 \pm 9.6 \rightarrow 61.1 \pm 9.6$ and GSRS score from $1.64 \pm 0.42 \rightarrow 1.24 \pm 0.15$ in 3 months. PET-CT after 3 months found partial contraction in one patient, but no change in two patients. One patient left the ketogenic diet after the 3 month evaluation as cranial metastasis was found, but elimination of tumor was found with γ knife procedure, and contraction of the primary tumor with erlotinib administration was found, then CR was reached with surgery. In one patient, erlotinib was continuously administered, and one patient was concurrently on multiple types of chemotherapy. All three patients were alive as of the priority date. One patient passed away thereafter prior to the filing date, but a significant life prolonging effect was observed. Further, analysis of the five patients by the Kaplan-Meier method revealed that there was a statistically significant difference at $p<0.05$ in the analysis as of the filing date (FIG. 11), and the dietary therapy of the invention has a significant effect. Existing cancer therapies are surgical resection, chemotherapy, and radiation therapy. The therapeutic effect by chemotherapy is not considered sufficient for lung cancer, pancreatic cancer and the like. Since ketogenic diet was demonstrated to have the potential to improve life prognosis against such advanced cancer, it is considered possible to develop a dietary therapy that is effective for cancer patients. Thus, the dietary therapy of the invention can be considered a supportive care for practicing one or more of the there major therapies (surgery, radiation therapy, and anticancer drug (chemotherapy)).

In another test example of the clinical study, the available carbohydrate restricted high fat diet of the invention was practiced for 3 months by recurrent breast cancer patients. This practice was for only 3 months, but a significant decrease in tumor markers was, still observed from the early stages of the therapy period by practicing the available carbohydrate restricted high fat diet of the invention. Surprisingly, a significant decrease in tumor markers was observed, and observation found recovery from cancer by simply practicing an early-stage (introductory-stage) therapy. As there was this much effect up to a fifth time in a patient with a sixth recurrence, this suggest, judging from tumor markers, that the dietary therapy of the invention is successful regardless of other anticancer therapy, which in turn suggests that introduction of dietary therapy alone can be successful. Further, prognosis during the introductory stage already shows improvement, which suggests that an introductory-stage treatment (dietary therapy) alone would also succeed.

Another test example of the clinical study confirmed the usefulness of ketogenic diet in cancer patients other than lung cancer patients (aforementioned five cases). The disease background was two patients with lung cancer, one patient with recurrence of uterine body cancer, one patient with recurrence of bladder cancer, one patient with a second recurrence of ovarian cancer, and one patient with a fourth recurrence of peritoneal cancer. Of the two lung cancer patients, one had nausea, and the other had a transformation from adenocarcinoma to small cell cancer during therapy, so that therapy was discontinued. Therapy for one patient with bladder cancer was discontinued due to an adverse event involving another cancer therapy. In the discontinued bladder cancer case, the subject passed away immediately thereafter. The discontinued therapy for two lung cancer patients also had extremely unfavorable prognosis. These no treatment groups can be evaluated as comparative examples. There were three cases that could be evaluated as Examples. Blood ketone bodies exhibited an increasing trend in acetoacetic acid and β-H butyrate in one month. Hypoglycemia, nausea, fatigue or the like was not observed, and the GSRS score showed an improvement in 3 months. Systemic condition scale slightly worsened. PET-CT after 3 months showed SD (=stable disease) in the uterine body cancer case, and PR (=partial response) in the ovarian cancer and peritoneal cancer cases. One uterine body cancer patient had strong ascites upon introduction. However, after supplementing nutrition with mainly ketogenic formula, ascites improved from CP125 6815→4486 U/ml one month after the introduction of ketogenic diet, despite rapid exacerbation prior to the introduction of ketogenic diet. Improvement in tense ascites and decrease in pleural effusion were also observed, and QOL also improved, e.g., the patient was allowed to leave the hospital, but resumption of chemotherapy was denied, and the patient passed away after 4 months from the introduction. However, this uterine body cancer patient case can be medically evaluated as showing a significant effect compared to cases without practicing the present invention. Currently as of July 2016, the other two patients are alive. For the ovarian cancer case, complete cure surgery has been performed and cancer is currently in remission as of the filing of the present application. Of the three patients, two ovarian cancer and peritoneal cancer patients exhibited PR by introduction of ketogenic diet. Thus, ketogenic diet therapy was also safely practiced in patients with cancer other than lung cancer and breast cancer, and can be evaluated as exhibiting a life prolonging effect.

In view of the above, the present invention provides the following.

(Item 1)

A composition comprising high fat diet for treating cancer or a combination thereof.

(Item 2)

The composition or combination thereof of item 1, characterized in that fat in the high fat diet is about 120 g or greater per day based on a real body weight of 50 kg, or about 70% or greater of daily total energy.

(Item 3)

The composition or combination thereof of item 1 or 2, characterized in that available carbohydrate is restricted in the high fat diet.

(Item 4)

The composition or combination thereof of item 3, characterized in that the high fat diet restricts carbohydrate to 30 g or less per day.

(Item 5)

The composition or combination thereof according to any one of items 1 to 4, characterized in that daily caloric intake in the high fat diet is 20 kcal/kg body weight or greater.

(Item 6)

The composition or combination thereof according to any one of items 1 to 5, wherein the high fat diet comprises about 60% (w/w) or greater of fat.

(Item 7)

The composition or combination thereof of item 6, wherein the high fat diet comprises about 0% (w/w) to about 15% (w/w) of carbohydrate.

(Item 8) The composition or combination thereof of item 6 or 7, wherein the high fat diet comprises about 10% (w/w) to about 20% (w/w) of protein.

(Item 9)

The composition or combination thereof according to any one of items 1 to 8, comprising a medium chain fatty acid oil (MCT oil).

(Item 10)

The composition or combination thereof according to any one of items 6 to 9, wherein the high fat diet comprises about 25% (w/w) to about 40% (w/w) of a long chain fatty acid oil, about 35% (w/w) to about 50% (w/w) of a medium chain fatty acid oil (MCT oil), about 0% (w/w) to about 15% (w/w) of carbohydrate, and about 10% (w/w) to about 20% (w/w) of protein.

(Item 11)

The composition or combination thereof according to any one of items 6 to 10, wherein the high fat diet comprises a ketogenic formula.

(Item 12)

The composition or combination thereof of item 9, wherein the medium chain fatty acid oil is comprised of a fatty acid with 8 to 11 carbons.

(Item 13)

The composition or combination thereof according to any one of items 7 to 12, wherein the carbohydrate comprises lactose.

(Item 14)

The composition or combination thereof according to any one of items 1 to 13, characterized by being combined with another therapy.

(Item 15)

The composition or combination thereof of item 14, wherein the another therapy comprises a surgical therapy, a chemotherapy, a radiation therapy, or a combination thereof.

(Item 16)

The composition or combination thereof according to any one of items 1 to 15, wherein the cancer is selected from the group consisting of non-small cell pulmonary malignant tumor, breast cancer, uterine body cancer, ovarian cancer, and peritoneal cancer.

(Item 17)

The composition or combination thereof according to any one of items 1 to 15, characterized in that the high fat diet is modified Atkins diet, which is 1) for the first week, provided at about 1500 kcal and at a ratio of about 140 g of lipid:about 60 g of protein:about 10 g of carbohydrate, based on a real body weight of 50 kg.

2) from the second week to the third month, provided at daily intake of carbohydrate of about 20 g or less, a daily calorie of about 1400 to about 1600 kcal, and at a ratio of about 120 to about 140 g of lipid:about 70 g of protein:about 20 g of carbohydrate; and 3) after the third month, provided at daily intake of about 30 g or less when intake of carbohydrate is about 10 g/intake, and is provided in accordance with 2) with respect to others.

(Item 18)

The composition or combination thereof of item 17, wherein the modified Atkins diet is provided by a ketogenic formula and/or an MCT oil.

(Item 19)

The composition or combination thereof according to any one of items 1 to 18, wherein a patient of the cancer has a performance status (PS) of 2 or lower.

(Item 20)

The composition or combination thereof according to any one of items 1 to 19, wherein a patient of the cancer does not have a diabetes complication.

(Item 21)

A composition or combination thereof for enhancing an effect of a cancer therapy, comprising high fat diet.

(Item 22)

The composition or combination thereof according to any one of items 1 to 21, wherein the composition or combination thereof is a food product.

(Item 23)

The composition or combination thereof of item 22, wherein the food product is selected from the group consisting of a frozen food product, a dairy product, a chilled food product, a nutritional food product, liquid food, nursing food, and a beverage.

(Item A1)

A composition for treating cancer, comprising fat at about 60% (w/w) or greater, or about 75% or greater of total energy.

(Item A2)

The composition of item A1, comprising about 0% (w/w) to about 15% (w/w) of carbohydrate.

(Item A3)

The composition of item A1 or A2, comprising protein at about 5% (w/w) to about 40% (w/w), or at 2% to 25% of total energy.

(Item A4)

The composition according to any one of items A1 to A3, wherein about 30% (w/w) or greater of the fat is an MCT oil.

(Item A5)

The composition according to any one of items A1 to A4, wherein the carbohydrate comprises lactose.

(Item A6)

The composition according to any one of items A1 to A5, comprised of a ketogenic formula.

(Item A7)

The composition according to any one of items A1 to A6, wherein the composition is a food product.

(Item B1)

A composition or a combination thereof for treating cancer, comprising available carbohydrate restricted diet.

(Item B2)

The composition or combination thereof of item B1, characterized in that the available carbohydrate restricted diet restricts carbohydrate to 30 g or less per day.

(Item B3)

The composition or combination thereof of item B1 or B2, wherein the available carbohydrate restricted diet comprises about 0% (w/w) to about 15% (w/w) of carbohydrate.

(Item B4)

The composition or combination thereof, according to any one of items B1 to B3, wherein the carbohydrate comprises lactose.

(Item B5)

The composition or combination thereof according to any one of items B1 to B4, wherein the composition or combination thereof is a food product.

(Item C1)

A composition for treating cancer, comprising a medium chain fatty acid oil (MCT oil).

(Item C2)

The composition of item C1, wherein the MCT oil is comprised of a fatty acid with 8 to 10 carbons.

(Item C3)

The composition of item 1 or 2, comprising about 30% (w/w) or greater of an MCT oil.

(Item C4)

The composition according to any one of items C1 to C3, wherein the composition is a food product.

(Item D1)

A dietary therapy by high fat diet for treating cancer, the high fat diet being modified Atkins diet, the modified Atkins diet comprising:

1) for the first week, providing about 1500 kcal at a ratio of about 140 g of lipid:about 60 g of protein:about 10 g of carbohydrate, based on a real body weight of 50 kg;

2) from the second week to the third month, providing daily intake of carbohydrate of about 20 g or less and a daily calorie of about 1400 to about 1600 kcal at a ratio of about 120 to about 140 g of lipid:about 70 g of protein:about 20 g of carbohydrate; and 3) after the third month, providing daily intake of about 30 g or less when daily intake of carbohydrate is about 10 g/intake, and providing the modified Atkins diet in accordance with 2) with respect to others.

In the present invention, one or more of the features described above are intended to be provided not only as the explicitly described combinations, but also as other combinations thereof. Additional embodiments and advantages of the present invention are recognized by those skilled in the art by reading and understanding the following detailed description, as needed.

One intended therapeutic form, for example, targets patients who have stage IV non-small cell pulmonary malignant tumor with PS of 0 to 1 and are capable of oral ingestion, and enables concurrent use of chemotherapy, radiation therapy, or the like. In addition, cancer targeted by the present invention includes colon carcinoma (colon cancer), breast cancer, uterine body cancer, bladder cancer, ovarian cancer, peritoneal cancer, rectal cancer, liver cancer, labial gland-like cystic cancer, metastasis of such cancer (liver metastasis, bone metastasis, and the like), recurrent cancer, and the like. The goal of ketogenic diet is 1) for the first week, calorie of 30 kcal/kg based on real body weight, no restriction in lipid, no restriction on protein, and 10 g or less of carbohydrate. Specifically, for the early stage of introduction, daily calorie is about 1500 kcal based on a real body weight of 50 kg and the ratio is about 140 g of lipid:about 60 g of protein:about 10 g of carbohydrate. The target ketogenic ratio (lipid/(protein+carbohydrate)) is 2:1. Other nutrients can be ingested without restriction. Required trace amounts of elements or vitamins are appropriately ingested using a supplement or the like. 2) for the second week to the third month, the goal is, based on the blood ketone body value, daily intake of carbohydrate of about 20 g or less, daily calorie of about 1400 to about 1600 kcal, a ratio of about 120 to about 140 g of lipid:about 70 g of protein:about 20 g of carbohydrate, and a ketogenic ratio of 2:1 to 1:1. MCT oil or ketogenic formula is used for supplementing calories. 3) After the third month, a single intake of carbohydrate is about 10 g/day and daily intake is about 30 g or less, and other values are in accordance with 2). Blood ketone bodies can be more readily induced compared to conventional methods by using MCT oil or ketogenic formula for supplementing energy. It is preferable to exclude cancer patients who are incapable of oral ingestion, cancer patients who have a PS of 3 or greater, or patients with a diabetes complication.

In the present invention, one or more of the features described above are intended to be provided not only as the explicitly described combinations, but also as other combinations thereof. Additional embodiments and advantages of the present invention are recognized by those skilled in the art by reading and understanding the following detailed description, as needed.

Advantageous Effects of Invention

Ketogenic diet was introduced safely in cancer patients. Improvement in quality of life was also observed, and the possibility of exhibiting a life prolonging effect was also suggested. When concurrently used with an anticancer agent or radiation therapy, introduction of ketogenic diet can enhance the therapeutic effect and has the potential to reduce the number of administrations of anticancer agents or reduce the frequency of radiation therapy. This is understood to contribute to reduction in medical cost. It is also possible that nutritional therapy for all cancer patients, including terminal cancer patients, can potentially be fundamentally toppled to establish a completely novel nutritional therapy. The estimated number of cancer patients in 2015 according to the National Cancer Center Japan is 982,100. In view of the above, the economic effect of the present invention is immeasurable, as the present invention can be applicable to all patients.

BRIEF DESCRIPTION OF DRAWINGS

FIG. 9 shows blood data for 3 cases with continued ketogenic diet. The top row shows venous blood acetoacetic acid and the bottom row shows venous blood butyrate. Each graph shows error bars and the unit.

FIG. 13 shows a comparison of CT of case 8 before and after therapy (after 3 months).

FIG. 14 shows a comparison of PET-CT of case 11 before and after therapy (after 4 months).

FIG. 15 shows a comparison of PET-CT of case 11 before and after therapy (after 4 months).

FIG. 16 shows a comparison of PET-CT of case 11 before and after therapy (after 4 months).

FIG. 17 shows a comparison of PET-CT of case 12 before and after therapy (after 3 months).

FIG. 18 shows a comparison of PET-CT of case 12 before and after therapy (after 3 months).

FIG. 19 shows a comparison of PET-CT of case 12 before and after therapy (after 3 months).

DESCRIPTION OF EMBODIMENTS

Figure 1:
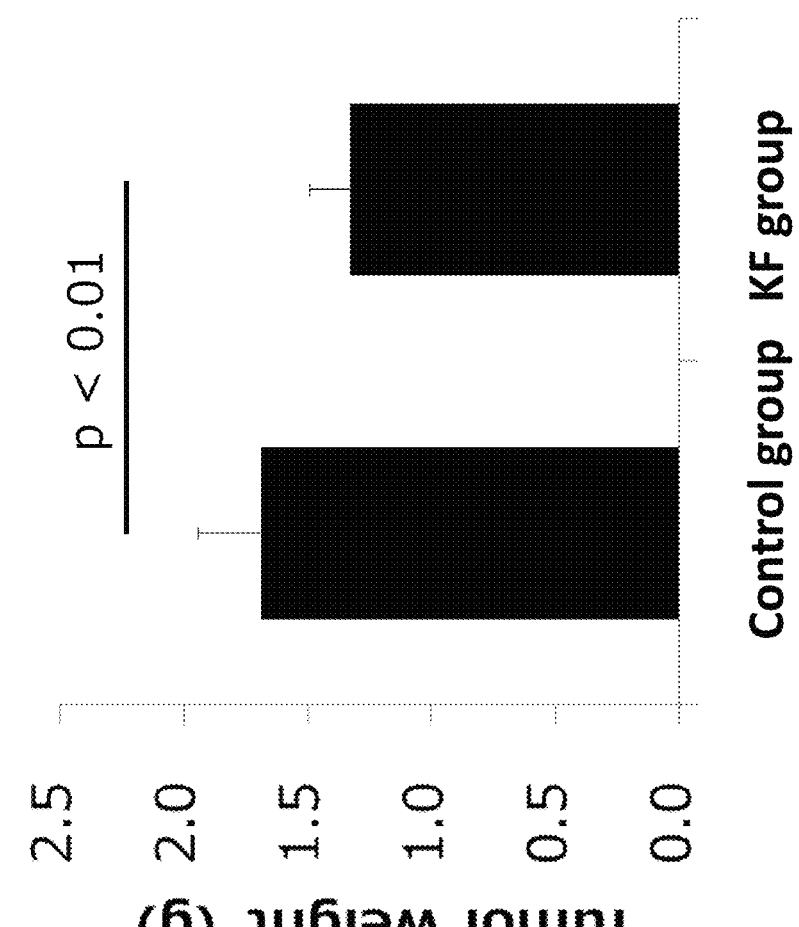
FIG. 1 shows data for tumor weight on day 21 after tumor transplant in the control group and the KF group.

The present invention is explained hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form unless specifically noted otherwise. Further, the terms used herein should be understood as used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

According to a report of the Ministry of Health, Labour and Welfare, high fat diet is determined by the relationship of carbohydrate and protein, as a proportion of total energy. According to the 2005 and 2006 National Health and Nutrition Survey [Kokumin Kenko Eiyo Chosa]2,3), high fat diet generally refers to intake of 30% or more of total energy from lipids when 1 g is calculated as 9 kcal. In a specific embodiment, high fat diet comprises fat at about 50% or greater of total energy, about 55% or greater of total energy, about 60% or greater of total energy, about 65% or greater of total energy, about 70% or greater of total energy, about 75% or greater of total energy, about 80% or greater of total energy, about 85% or greater of total energy, or about or 90% or greater of total energy amount. In a preferred embodiment, high fat diet comprises fat at about 80% or greater of total energy. In another embodiment, daily fat intake based on a real body weight of 50 kg is about 80 g or greater, about 90 g or greater, about 100 g or greater, about 110 g or greater, about 115 g or greater, about 120 g or greater, about 125 g or greater, about 130 g or greater, about 135 g or greater, about 140 g or greater, about 145 g or greater, or about 150 g or greater. In another preferred embodiment, the daily fat intake based on a real body weight of 50 kg is about 140 g or greater. Available carbohydrate is preferably restricted in high fat diet (i.e., available carbohydrate restricted high fat diet).

Fat contained in high fat diet can be short chain fatty acid oil, medium chain fatty acid oil, long chain fatty acid oil, or a combination thereof. Fat contained in high fat diet preferably has a high ratio of medium chain fatty acid oil. Specifically, medium chain fatty acid oil is about 10% or greater, about 20% or greater, about 30% or greater, about 40% or greater, about 50% or greater, about 60% or greater, about 70% or greater, or about 80% or greater of fat contained in high fat diet.

As used herein, "medium chain fatty acid oil" refers to oil having constituent fatty acids of oil and fat with a medium chain length, which is also called MCT (Medium Chain Triglyceride), and typically refers to oil comprised of fatty acids with 6 to 12 carbons, preferably fatty acids with 8 to 12 carbons, or fatty acids with 8 to 10 carbons. Medium chain fatty acid oil is more readily digested, absorbed, and converted to energy than common oil. Examples thereof include hexanoic acid (caproic acid; C6), octanoic acid (caprylic acid; C8), nonanoic acid (pelargonic acid; C9), decanoic acid (capric acid; C10), and dodecanoic acid (lauric acid; C12).

As used herein, "available carbohydrate restricted high fat diet" (so called "ketogenic diet") refers to diet with less intake of available carbohydrate and more fat than normal diet (i.e., aforementioned high fat diet with available carbohydrate restriction further added thereto). Generally, available carbohydrate restriction refers to a daily available carbohydrate intake of 100 g or less. This numerical value was calculated based on the following portion of the 2010 nutrition report of the Ministry of Health, Labour and Welfare: "If it is assumed that the basal metabolic rate is 1,500 kcal/day, the energy consumption of the brain would be 300 kcal/day, corresponding to 75 g of glucose/day. Since tissue other than the brain also uses glucose as an energy source as discussed above, the required amount of glucose is estimated to be at least 100 g/day, i.e., the minimum required amount of readily digestible carbohydrate is estimated to be 100 g/day". Thus, it is understood that this value can vary. Ketogenic diet that can be used in the present invention is generally known to have an action of alleviating seizures of refractory epilepsy patients and action of alleviating glucose transporter type 1 deficiency or pyruvate dehydrogenase complex abnormality. Such diet is also confirmed to be safe. Ketogenic formula (Meiji 817-B; Meiji Co., Ltd.) is an example of ketogenic diet.

The term "carbohydrate" used herein refers to an organic compound with a monosaccharide as a constituent component. "Carbohydrate" as used in the context of high fat diet, available carbohydrate restricted diet, available carbohydrate restricted high fat diet, or the like refers to available carbohydrate, and "carbohydrate" and "available carbohydrate" are interchangeably used. The term "available carbohydrate" used herein refers to carbohydrate that is not dietary fiber, including monosaccharides, disaccharides, and polysaccharides. Examples of monosaccharides include glucose (grape sugar), fructose (fruit sugar), galactose, and the like. Examples of disaccharides include maltose (malt sugar), sucrose (saccharose), lactose (milk sugar), and the like. Examples of polysaccharides include starch (amylose and amylopectin), glycogen, dextrin, and the like.

As used herein, "available carbohydrate restricted high fat diet" generally refers to diet with daily available carbohydrate intake of about 100 g or less and lipid intake of about 30% or greater of total energy intake.

In a preferred embodiment, daily available carbohydrate intake can be about 90 g or less, about 80 g or less, about 70 g or less, about 60 g or less, about 50 g or less, about 40 g or less, about 35 g or less, about 30 g or less, about 25 g or less, about 20 g or less, about 15 g or less, or about 10 g or less. Preferably, high fat can be about 35% or greater, about 40% or greater, about 45% or greater, about 50% or greater, about 55% or greater, about 60% or greater, about 65% or greater, about 70% or greater, about 75% or greater, or about 80% or greater of total energy intake.

In a preferred embodiment, available carbohydrate restricted high fat can be determined from the ketogenic ratio (lipid/(protein+carbohydrate)) (weight ratio). A ketogenic ratio equal to or greater than about 1:about 1 (more lipid) is preferable as available carbohydrate restricted high fat diet. The ratio may be about 1:about 1 or any ratio with more lipids. However, in one embodiment, the ratio may be set to about 1:about 1 to about 2:about 1 and preferably around 2:1 upon introduction. The amount of protein and carbohydrate may be any amount, as long as the ketogenic ratio meets the definition, but is preferably about 30 g or less per day, more preferably about 20 g or less per day, and still more preferably about g or less per day, or may be a combination thereof depending on the timing. The amount of a single intake may be in any range, as long as it is within the daily intake, but is preferably about 10 g or less per intake. Although not wishing to be bound by any theory, about 60 to about 90% of energy intake is taken with fat. Available carbohydrate restricted high fat diet can be provided by, for example, ketogenic formula (Meiji 817-B; Meiji Co., Ltd.) When used for children, Atkins diet may be used, and modified Atkins diet may be used for adults. Modified Atkins diet is the following. 1) For the first week, the goal is calorie of about 30 kcal/kg based on real body weight, no restriction on fat, no restriction on protein, and about 10 g or less of carbohydrate. Specifically, for the early stages of introduction, the goal is 1) daily calorie of about 1500 kcal and a ratio of about 140 g of lipid:about 60 g of protein:about 10 g of carbohydrate based on a real body weight of 50 kg. The target ketogenic ratio (lipid/(protein+carbohydrate)) is 2:1. Other nutrients can be ingested without restriction. Required trace amounts of elements or vitamins are appropriately ingested using a supplement or the like. 2) for the second week to the third month, the goal is, based on the blood ketone body value, daily intake of carbohydrate of about 20 g or less, daily calorie of about 1400 to about 1600 kcal, a ratio of about 120 to about 140 g of lipid:about 70 g of protein:about 20 g of carbohydrate, and a ketogenic ratio of 2:1 to 1:1. MCT oil or ketogenic formula is used for supplementing calories. 3) After the third month, a single intake of carbohydrate is about 10 g/day and daily intake is about 30 g or less, and other values are in accordance with 2).

In another preferred embodiment, the high fat diet of the invention (e.g., available carbohydrate restricted high fat diet) comprises about 60% (w/w) or greater of fat, about 0% (w/w) to about 15% (w/w) of carbohydrate, and about 10% (w/w) to about 20% (w/w) of protein. In a more preferred embodiment, the high fat diet of the invention (e.g., available carbohydrate restricted high fat diet) comprises about 25% (w/w) to about 40% (w/w) of a long chain fatty acid oil, about 35% (w/w) to about 50% (w/w) of a medium chain fatty acid oil (MCT oil), about 0% (w/w) to about 15% (w/w) of carbohydrate, and about 10% (w/w) to about 20% (w/w) of protein. In a still more preferable embodiment, the high fat diet of the invention (e.g., available carbohydrate restricted high fat diet) comprises a ketogenic formula or a composition comprised of a main ingredient that is equivalent thereto. The main composition of a ketogenic formula (Meiji 817-B; Meiji Co., Ltd.) is shown in the following Table 1.

TABLE 1

| Composition | In 100 g of ketogenic formula (% E) |
|---|---|
| Protein | 15.0 g (8.1) |
| Lipid | 71.8 g (87.2) |
| Carbohydrate | 8.8 g (4.7) |
| Ash | 2.4 g (0) |
| Moisture | 2.0 g (0) |

[Remarks]
Protein: milk protein
Lipid: 32.1 g (39.0% E) of long chain fatty acid oil and fat (required fatty acid adjusting fat) 39.7 g (48.2% E) of medium chain fatty acid-oil and fat
Carbohydrate: lactose
% E: % energy In addition to the aforementioned main ingredients, a ketogenic formula comprises vitamin A, vitamin B1, vitamin B2, vitamin B6, vitamin B12, vitamin C, vitamin D, vitamin E, vitamin K, pantothenic acid, niacin, folic acid, calcium, magnesium, sodium, potassium, phosphorous, chlorine, iron, copper, and zinc.

In a preferred embodiment, the available carbohydrate restricted high fat diet of the invention advantageously avoids low calorie diet (e.g., diet of less than 1000 kcal/day such as 600 kcal/day). This is because the prognostic condition of a patient is not favorable when low calorie diet is added. It is understood that it is important for cancer therapy to maintain a certain level of calories. For example, daily caloric intake is preferably not below the basal metabolic rate. The basal metabolic rate can be calculated based on the real body weight of the target patient using an equation known in the art or the like. For example, according to Dietary Reference Intakes for Japanese (2015) published by the Ministry of Health, Labour and Welfare, the rate is 21.5 kcal/kg body weight/day for males who are 50 years old or older and 21.5 kcal/kg body weight/day for females who are 50 years old or older, but is 24.0 kcal/kg body weight/day for males who are 18 to 29 years old and 22.1 kcal/kg body weight/day for females who are 18 to 29 years old.

Some diet with available carbohydrate of about 60 to about 70 g/day is also referred to as ketogenic diet in the art, but available carbohydrate is preferably restricted to about 30 g/day or less. Although not wishing to be bound by any theory, restriction of available carbohydrate to about g/day or less can induce blood ketone bodies (acetoacetic acid and β-hydroxybutyrate). This result improves the prognosis of cancer patients.

Unless specifically noted otherwise, the number of grams of daily intake of fat, carbohydrate or protein described herein is based on a real body weight of 50 kg. As used herein, "real body weight" refers to the actual body weight. Those skilled in the art understand that the number of grams of daily intake can vary for different real body weights. For example, it is understood that the intake, when the real body weight is 80 kg, is 1.6-times the intake based on a real body weight of 50 kg.

As used herein, "cancer" includes, for example, tumor developed from a mutation of a normal cell. Malignant tumor can develop from any organ or tissue of the entire body. Unless specifically distinguished, "cancer" is used synonymously with "malignant tumor". For example, cancer includes one or more selected from lung cancer, esophageal cancer, gastric cancer, liver cancer, pancreatic cancer, renal cancer, adrenal cancer, bile duct cancer, breast cancer, colon cancer, small intestine cancer, ovarian cancer, uterine cancer, uterine body cancer, endometrial cancer, bladder cancer, prostate cancer, ureter cancer, renal pelvis cancer, ureter cancer, penile cancer, testicular cancer, brain tumor, central nervous system cancer, peripheral nervous system cancer, head and neck cancer, glioma, glioblastoma multiforme, skin cancer, melanoma, thyroid cancer, salivary gland cancer, malignant lymphoma, carcinoma, sarcoma, leukemia, and hematological malignancy. Lung cancer includes; for example, non-small cell lung cancer (e.g., adenocarcinoma, squamous cell carcinoma, large cell cancer, and the like) or small cell lung cancer. In a preferred embodiment, the present invention is characterized by being able to treat patients with terminal cancer, including advanced cancer, metastatic cancer, and the like. Especially in terminal cancer patients, the prognosis is markedly improved, with some cases resulting in remission. Such an effect was not observed in conventional diet therapy or common cancer therapy.

As used herein, "metastasis" refers to the process of cancer spreading or migrating from the primary site in the body to another region to develop a similar cancerous lesion at a new location. "Metastatic" or "metastasizing" cells are cells that lose adherent contact with adjacent cells and move from the primary site of a disease through blood flow or lymph to enter a nearby body structure. As used herein, the term metastasis preferably includes, but is not limited to, metastasis of the cancer described herein, more preferably metastasis of solid cancer, and more preferably metastasis of cancer selected from the group consisting of breast, heart, lung, small intestine, colon, spleen, kidney, bladder, head and neck, ovarian, prostate, brain, pancreatic, skin, bone, thymic, uterine, testicular, cervical and/or liver cancer.

The present invention can treat cancer at any degree of advancement and any type of cancer.

For example, cancer can be classified as follows according to TNM classification.
Primary Tumor (T: Tumor):
  T0=no tumor (no solid formation)
  T1 to T4=cancer classified by each organ depending on the size and extent of infiltration
Lymph Node Metastasis (N: Lymph Nodes):
  N0=no lymph node metastasis
  N1 to N4=classified by each organ depending on the degree of lymph node metastasis
Distant Metastasis (M: Metastasis)
  M0=no distant metastasis
  M1=with distant metastasis
In addition, stage classification was established so that the degree of advancement and spread of cancer can be represented at once based on the TNM classification. Stage classification can also be used herein as an indicator of the degree of advancement. Since this is a classification in line with clinical practice, this is also called clinical advancement stage classification.

TABLE 1A

| Stage 0 | Tis (intraepithelial carcinoma) to T1 | N0 | M0 |
|---|---|---|---|
| Stage I | T1 to T2 | N0 to N1 | M0 |
| Stage II | T1 to T3 | N0 to N2 | M0 |
| Stage III | T2 to T4 | N0 to N2 | M0 |
| Stage IV | T4 | N2 | M0 to M1 |

Although not wishing to be bound by any theory, the present invention provides therapy with a therapeutic effect that improves, without impairing the prognosis, various types of cancer or cancer at various stages (including early stage and terminal cancer) and improves QOL, to the extent that some cases result in remission.

In a preferred embodiment, the composition or combination thereof or dietary therapy of the invention is preferably combined with another therapy. Any therapy may be used as another therapy, as long as it is used as therapy for cancer. Examples thereof include surgical therapy (e.g., resection/extraction) chemotherapy, radiation therapy, and the like.

Surgical therapy refers to resection of a cancer lesion, and in case of metastasis to the surrounding tissue or lymph node of the organ, excision thereof with the lesion or extraction of the organ itself. If resection is possible, surgical therapy is proactively used for early stage cancer or somewhat advanced cancer. A method that minimizes the resected region as much as possible (reduction surgery), laparoscopic surgery using an endoscope (miniature camera), thoracoscopic surgery and the like have been developed, which are encompassed by surgical therapy.

Chemotherapy is a therapeutic method that mainly kills cancer cells or suppresses the growth thereof with an anticancer agent. The method of administering an anticancer agent includes IV drip, injection, oral ingestion, and the like. Since an anticancer agent systemically circulates through blood, it also has an effect on very small metastasis. Hormonal therapy (endocrine therapy) is also sometimes encompassed by chemotherapy.

Radiation therapy is a local therapy that irradiates radiation on a cancer lesion to kill cancer cells. With the advancement in the pre-therapy testing techniques and irradiation methods, it is possible to accurately measure the size and position of cancer and localize the irradiation only to the cancerous portion. Radiation therapy includes not only "external irradiation" that irradiates radiation from the outside of the body, but also "brachytherapy" that inserts a needle or a capsule with a radiation emitting substance sealed therein into a lesion, and "radionuclide therapy" that administers a radioactive substance by injection or oral administration. X-rays are often used as the radiation used in radiation therapy, but proton beam therapy or heavy ion beam (carbon ion beam) therapy using particle beams can also be used.

It is understood that each of the therapies can be combined with the dietary therapy of the invention.

In one specific Example, cancer targeted by the present invention includes non-small cell pulmonary malignant tumor (e.g., pulmonary adenocarcinoma), colon carcinoma (colon cancer), breast cancer, uterine body cancer, bladder cancer, ovarian cancer, peritoneal cancer, rectal cancer, liver cancer, labial gland-like cystic cancer, metastasis of such cancer (liver metastasis, bone metastasis, and the like), recurrent cancer, and the like. However, as demonstrated herein, specific examples are not limited thereto. It is understood that any cancer and malignant tumor are encompassed thereby. In another specific embodiment, cancer targeted by the present invention includes Stage IV cancer such as non-small cell pulmonary malignant tumor (e.g., pulmonary adenocarcinoma). Such late stage cancer is also encompassed as specific examples.

Preferred Embodiment

The preferred embodiments of the present invention are explained hereinafter. It is understood that the embodiments provided hereinafter are provided to better facilitate the understanding of the present invention, so that the scope of the present invention should not be limited to the following description. Thus, it is apparent that those skilled in the art can refer to the descriptions herein to appropriately make modifications within the scope of the present invention. It is also understood that the following embodiments of the present invention can be used individually or as a combination.

(Cancer Therapy by High Fat Diet)

In one aspect, the present invention provides a composition or a combination thereof for treating cancer, comprising high fat diet. The present invention can introduce high fat diet to treat cancer of a wide range of types and degrees of advancement, including terminal cancer that has been very difficult to treat to remission, and achieve remission in some cases.

In one embodiment, fat in the high fat diet of the invention is about 80 g or greater, about 90 g or greater, about 100 g or greater, about 110 g or greater, about 120 g or greater, about 120 g or greater, about 125 g or greater, about 130 g or greater, about 135 g or greater, or about 140 g or greater per day, based on a real body weight of 50 kg. More specifically, fat in the high fat diet of the invention is about 80 g to about 180 g per day, preferably about 90 g to about 170 g per day, more preferably about 100 g to about 160 g per day, still more preferably about 110 g to about 150 g per day, and most preferably about 120 g to about 140 g per day, based on a real body weight of 50 kg.

In another embodiment, fat in the high fat diet of the invention is about 50% or greater of total energy, about 55% or greater of total energy, about 60% or greater of total energy, about 65% or greater of total energy, about 70% or greater of total energy, about 75% or greater of total energy, about 80% or greater of total energy, about 85% or greater of total energy, or about or 90% or greater of total energy. More specifically, fat in the high fat diet of the invention is about 50% to about 95% of total energy, preferably about 60% to about 90% of total energy, more preferably about 65% to about 85% of total energy, and most preferably about 70% to about 80% of total energy.

In a preferred embodiment, available carbohydrate is restricted in high fat diet, i.e., high fat diet is characterized by being available carbohydrate restricted high fat diet. The available carbohydrate restricted high fat diet of the invention is characterized in that carbohydrate is restricted to about 30 g or less per day. Examples of available carbohydrate restriction include restriction to about 60 to about 70 g/day. Although not wishing to be bound by any theory, improvement in prognosis is expected by further restricting this amount. Thus, it is understood that an improved therapeutic effect compared to conventional diet can be achieved. In a preferred embodiment, available carbohydrate restriction during the introductory stage may be further restricted to about 20 g per day or less, and more preferably about 10 g/day or less. Further limitation of available carbohydrate restriction during the introductory stage can rapidly induce blood ketone bodies (acetoacetic acid or β-hydroxybutyrate), resulting in improved prognosis of cancer patients. However, diet during the early stages of introduction is different from conventional dietary habits, so that it is difficult to continue the diet. Gradually relaxation of the restriction on available carbohydrate intake allows continuation of available carbohydrate restricted high fat diet, and a therapeutic effect is also observed by doing so. This is because the above two revolutionary effects are expected. Thus, the restricted amount of available carbohydrate (carbohydrate intake) is not limited to about 10 g/day→about 20 g/day→about 30 g/day, or the like, as long as the amount is characterized by an initial amount with a strict restriction (e.g., about 10 g/day or less) that is gradually relaxed therefrom. Thus, the initially introduced amount can be optionally started, for example, at about 5 to about 15 g/day or thereabouts (±about 5 g/day), and the amount can be maintained at about 15 to about 25 g/day or thereabouts (±about 5 g/day) in the second stage, and can continue to be about 25 to about 35 g/day or thereabouts (±10 g/day) in the last maintenance stage.

Under available carbohydrate restriction (e.g., aforementioned daily available carbohydrate intake), available carbohydrate restricted high fat diet may contain a monosaccharide such as glucose (grape sugar), fructose (fruit sugar), galactose, or the like, disaccharide such as maltose (malt sugar), sucrose (saccharose), lactose (milk sugar), or the like, polysaccharide such as starch (amylose or amylopectin), glycogen, dextrin, or the like, or any combination thereof. In another embodiment, available carbohydrate restricted high fat diet does not contain glucose or a polysaccharide having glucose as a basic constituent element. Under available carbohydrate restriction (e.g., aforementioned daily available carbohydrate intake), available carbohydrate restricted high fat diet preferably comprises lactose (milk sugar). In another preferred embodiment, it is preferable to comprise lactose (milk sugar) but not glucose as available carbohydrate. In another preferred embodiment, it may be preferable to substantially comprise only lactose (milk sugar) as available carbohydrate. Although, not wishing to be bound by any theory, this is because improvement in prognosis or an effect of tumor contraction is expected. In an embodiment comprising milk sugar in available carbohydrate restricted high fat diet, about 10% or greater, about 20% or greater, about 30% or greater, about 40% or greater, about 50% or greater, about 60% or greater, about 70% or greater, about 80% or greater, or about 90% or greater of total available carbohydrate is lactose, and preferably all available carbohydrate is lactose.

(Available Carbohydrate Restricted Diet)

Another aspect provides a composition or a combination thereof for treating cancer, comprising available carbohydrate restricted diet. Available carbohydrate restricted diet refers to diet with lower available carbohydrate intake relative to normal diet. For example, available carbohydrate restricted diet restricts carbohydrate to about 30 g or less per day. Alternatively, available carbohydrate restricted diet comprises about 0% (w/w) to about 15% (w/w) of carbohydrate. The composition or combination thereof of the invention is not limited to the aforementioned carbohydrate intake, and may have any characteristic shown above or below.

(Composition Comprising MCT Oil)

Still another aspect provides a composition for treating cancer, comprising a medium chain fatty chain oil (MCT oil). For example, the composition of the invention comprises an about 30% (w/w) or greater of MCT oil and/or the MCT oil is comprised of a fatty acid with about 8 to about 10 carbons. The composition of the invention can have any characteristic shown above or below.

(Caloric Intake)

In a still more preferred embodiment, the high fat diet, available carbohydrate restricted diet, or available carbohydrate restricted high fat diet of the invention is characterized in that daily caloric intake is about 20 kcal/kg body weight or greater (about 1000 kcal or greater at a standard weight of 50 kg). Although not wishing to be bound by any theory, this is because prognosis can be improved by avoiding low calorie (e.g., about 600 kcal/day based on a standard body weight of 50 kg). Thus, the diet can be utilized in some cases at 20 kcal/kg body weight/day or less, such as about 14 kcal/kg body weight/day or greater, about 16 kcal/kg body weight/day or greater, or about 18 kcal/kg body weight/day, or preferably about 22 kcal/kg body weight/day or greater, about 24 kcal/kg body weight/day or greater, about 26 kcal/kg body weight/day or greater, about 28 kcal/kg body weight/day or greater, or the like, and the diet can be utilized at about 30 kcal/kg body weight/day in a representative example (Preferred Composition, Component, and Intake Form)

In a preferred embodiment, the high fat diet, available carbohydrate restricted diet, or available carbohydrate restricted high fat diet of the invention is provided as a ketogenic formula (Meiji 817-B; Meiji Co., Ltd.) or a altered product thereof (e.g., product with available carbohydrate and/or protein further reduced (e.g., product with each component independently changed ±about 5%, ±about 10%, ±about 15%, ±about 20%, or ±about 25%)). Thus, the present invention provides a ketogenic formula (or composition with composition equivalent thereto) or a altered product thereof for treating cancer.

In another preferred embodiment, the high fat diet, available carbohydrate restricted diet, or available carbohydrate restricted high fat diet of the invention comprises a medium chain fatty acid oil. Any medium chain fatty acid oil that is utilized in the art can be used as the medium chain fatty acid oil to be used. Typically, medium chain fatty acid oil comprised of a fatty acid with 6 to 12 carbons, preferably a fatty acid with 8 to 12 carbons, or a fatty acid with 8 to 10 carbons can be utilized. For example, Nissin MCT oil and powder, extra virgin coconut oil or the like sold by Nissin Oillio can be used. A medium chain fatty acid oil (MCT oil) can be about 10% or greater, about 20% or greater, about 30% or greater, about 40% or greater, about 50% or greater, about 60% or greater, about 70% or greater, or about 80% or greater of fat contained in high fat diet. In another embodiment, medium fatty acid oil (MCT oil) is about 10% to about 90%, about 20% to about 80%, about 30% to about 80%, or about 40% to about 70% or preferably about 50% to about 60% of fat contained in high fat diet.

A preferred embodiment can use diet altered as modified Atkins diet. For example, 1) for the first week, the goal is calorie of 30 kcal/kg body weight based on the real body weight, no restriction on lipid, no restriction on protein, and 10 g or less of carbohydrate, specifically, for the early stages of introduction, 1) treatment can be administered with daily calorie of 1500 kcal based on a real body weight of 50 kg, a ratio of 140 g of lipid:60 g of protein:10 g of carbohydrate (ketogenic ratio (lipid/(protein+carbohydrate)) is 2:1), and other nutrients ingestible without restriction while required trace amounts of elements or vitamins are appropriately ingested using a supplement or the like. The period can be appropriately extended or shortened from several days to several weeks.

2) for the second week to the third month, diet is appropriately adjusted while referring to the blood ketone body value. For example, guidance is given so that acetoacetic acid is not 500 μmol/L or greater and β-hydroxybutyrate is not 1000 μmol/L or less, and the goal is, if possible, acetoacetic acid of 1000 μmol/L or greater and β-hydroxybutyrate of 2000 μmol/L or grater. The goal is daily intake of carbohydrate of 20 g or less, daily calorie of 1400 to 1600 kcal, a ratio of 120 to 140 g of lipid:70 g of protein:20 g of carbohydrate, and a ketogenic ratio of 2:1 to 1:1. MCT oil or ketogenic formula is used for supplementing calories. The period may be appropriately extended or shortened. 2 weeks may be slightly shifted ahead or behind, and the third month may also be slightly shifted ahead or behind (about 1, 2 or several weeks of shift is acceptable).

3) After the third month, a single intake of carbohydrate is 10 g/day and daily intake is 30 g or less, and other values are in accordance with 2). Since this is after 2), this itself would shift when the third month shifts.

Blood ketone bodies can be more readily induced compared to conventional methods by using MCT oil or ketogenic formula for supplementing energy. It is preferable to exclude cancer patients who are incapable of oral ingestion, cancer patients who have a PS of 3 or greater, and patients with a diabetes complication.

In one embodiment, the high fat diet, available carbohydrate restricted diet, or available carbohydrate restricted high fat diet of the invention may be combined with another therapy. Such another therapy may include surgical therapy, chemotherapy, radiation therapy, or a combination thereof. Although not wishing to be bound by any theory, the high fat diet, available carbohydrate restricted diet, or available carbohydrate restricted high fat diet of the invention has a property of assisting existing cancer therapies. Thus, the diet of the invention can be additionally practiced on patients who are already receiving therapy.

Thus in another aspect, the present invention provides a composition or combination thereof for enhancing an effect of cancer therapy, comprising high fat diet, available carbohydrate restricted diet, or available carbohydrate restricted high fat diet.

The high fat diet, available carbohydrate restricted diet, or available carbohydrate restricted high fat diet provided by the present invention is a combination of various modules. Thus, it is understood that such diet is not only provided as a narrowly-defined composition or combination thereof, but also as a kit or combination of various components (individual food).

(Food Product Composition or Combination Thereof)

In another aspect, the present invention provides a food product composition or a combination thereof for treating cancer, comprising high fat diet, available carbohydrate restricted diet, or available carbohydrate restricted high fat diet. In one embodiment, the composition or combination of the invention is provided as a food product. As used herein, "food product" refers to a natural product or a processed product thereof comprising one or more types of nutrients, including all beverages. For example, food products include lunch box forms and sets of meal forms provided at restaurants or as a catering service. "Food product" can be used in the meaning including feed when using mammals other than humans as the subject. Examples of food products include, but are not limited to, frozen food products, dairy products, chilled food products, nutritional food products, liquid food, nursing food, beverages, and the like. In another embodiment, a food product composition or a combination thereof may be provided by percutaneous endoscopic gastrostomy. This is because terminal cancer patients may be incapable of or struggle with oral ingestion of food. The food product composition or combination thereof of the invention may be prepared by adding an MCT oil and/or ketogenic formula. The dietary therapy of the invention can be practiced by providing a food product composition or a combination thereof that has nutrient composition adjusted in advance. The food product composition or combination thereof of the invention can have any characteristic discussed above or below herein.

(Other Forms)

In another aspect, the composition or combination thereof of the invention can be provided as a medicament, or a supplement or quasi drug in Japan. A nutrient that is insufficient with dietary therapy can be supplemented with a supplement or a quasi-drug. For example, insufficient fat can be additionally taken with a supplement in high fat diet. For supplements comprising fat, the contained fat is preferably medium chain fatty acid. In a specific embodiment, the composition or combination of the invention is preferably provided as a medicament. The composition or combination thereof of the invention can have any characteristic described above or below herein.

Cancer targeted by the present invention can be any cancer. For any cancer, patients who have or have not received therapy can be targeted. In addition, the type of cancer is not particularly limited. The stage or classification of cancer is also not particularly limited. Thus, the present invention is effective on types and stages of cancer that have been considered difficult to treat. Moreover, the present invention is significant in that the prognosis is excellent, and remission can be attained for types and stages of cancer for which remission was difficult or unattainable. In particular, the present invention is significant in that terminal cancer in stage IV or the like, metastatic or advanced cancer, or refractory cancer can also be targeted. For example, non-small cell pulmonary malignant tumor can be treated, and an example is demonstrated with a patient reaching remission. In particular, patients who did not receive the dietary therapy of the invention have unfortunately passed away, while all patients who had received the dietary therapy of the invention are still alive beyond expectations. Moreover, tumor has been eliminated in some patients. Such an effect was unexpected from conventional therapy. Although not wishing to be bound by any theory, it is understood that such an effect has been achieved by strictly restricting especially carbohydrate, setting calorie relatively high, and setting fat to a relatively high calorie %.

Patients in any condition can be targeted, but patients preferably have a performance status (PS) of 2 or lower. This is because they are patients on whom normal dietary therapy can be practiced without issue. In a preferred embodiment, it is advantageous, that target patients do not have a diabetes complication. This is because diabetes patients require separate restriction on available carbohydrate. However, it is understood that the cancer therapy of the invention can be concurrently used by appropriately restricting available carbohydrate to also be compatible for diabetes. Diabetes patients were excluded in the early clinical trial because safety was prioritized upon submission to the ethics committee. It has been confirmed that hypoglycemia does not occur with the supply of available carbohydrate from the muscle or liver, even with restriction on available carbohydrate. Thus, this can also be practiced on diabetes patients.

Any mammal can be used as a, target patient that can be used in the present invention. Examples thereof include rodents such as mice, rats, hamsters, and guinea pigs, Lagomorpha such as rabbits, ungulates such as pigs, cows, goats, horses, and sheep, Carnivoras such as dogs and cats, primates such as humans, monkeys, rhesus monkeys, cynomolgus monkeys, marmosets, orangutans, and chimpanzees, and the like. Mammals are preferably rodents (mice or the like) or primates (humans or the like), more preferably primates, and still more preferably humans.

Since the present invention is for example dietary therapy, it is orally ingested, but the present invention may be ingested by IV drip, percutaneous endoscopic gastrostomy, or the like. Thus, the composition or combination of the invention can also be provided as a transfusion.

Although the composition or combination thereof is generally ingested in three separate ingestions per day, it is understood that the frequency of ingestions may be twice daily, or 4 or 5 times daily. As discussed above, separate prescriptions are given for the introductory stage (generally the first week), transition stage (generally two weeks to three months), and maintenance stage (generally after three months), so that the ingestion method may be the same or appropriately changed.

Thus, the present invention also provides a method of treating or preventing a target disease (e.g., cancer) using the present invention (e.g., step of feeding high fat diet, available carbohydrate restricted diet, or available carbohydrate restricted high fat diet). In a method of treating or preventing cancer in an embodiment of the present invention, high fat diet, available carbohydrate restricted diet, or available carbohydrate restricted high fat diet can be expected to be fed alone, but it is generally fed in combination with another cancer therapy such as one of surgery, radiation therapy, and chemotherapy (anticancer agent) called the three major therapies or any combination thereof (including treatment with one or more anticancer agents for chemotherapy).

Thus, the therapy of the invention may be called supportive care when administered in combination with such other anticancer therapy.

The method of the invention comprises a step of feeding high fat diet, available carbohydrate restricted diet, or available carbohydrate restricted high fat diet discussed above. Another preferred embodiment can be appropriately applied in the method of the invention. The following is a representative dietary therapy.

The dietary therapy comprises:

1) a step of feeding diet for about the first week (period can be appropriately extended or shortened, which may be several days to several weeks) at calorie of about 30±10 kcal/kg body weight based on a real body weight, no restriction on lipid, no restriction on protein, and about 40 g or less, preferably 10 g or less, of carbohydrate, and preferably a daily calorie of about 1500±500 kcal based on a real body weight of 50 kg and a ratio of about 110 to 170 g of lipid:about 35 to 85 g of protein:about 10 to 40 g of carbohydrate (ketogenic ratio (lipid/(protein+carbohydrate)) is about 2±1:about 1), while other nutrients can be ingested without restriction and required trace amounts of elements or vitamins are appropriately ingested using a supplement or the like;

2) providing diet for about the second week to about the third month (the period may be appropriately extended or shortened and shifted ahead or behind of 2 weeks, and the third month may also be slightly shifted ahead or behind (about 1, 2 or several weeks of shift is acceptable)), preferably with an MCT oil or ketogenic formula, by giving guidance while referring to the blood ketone body value so that acetoacetic acid is not about 500±100 μmol/L or greater and β-hydroxybutyrate is not about 1000±200 μmol/L or less, with a goal of, if possible, acetoacetic acid of about 1000±200 μmol/L or greater and β-hydroxybutyrate of about 2000±400 μmol/L or grater, wherein the goal is daily intake of carbohydrate of about about 40 g or less, daily calorie of about 1200 to about 2000 kcal, and a ratio of about 90 to about 170 g of lipid:about 45 to 95 g of protein:about 10 to 40 g of carbohydrate, and a ketogenic ratio of about 2:1 to about 1:1; and 3) after the third month (the end of period of 2) itself would shift when the third month shifts), providing diet at a single intake of carbohydrate of about 30 g/day or less and daily intake of about 75 g or less and preferably 30 g or less, and providing the diet in accordance with 2) with respect to others.

In one embodiment, daily caloric intake is preferably not below the basal metabolic rate. The basal metabolic rate can be calculated based on the real body weight of the target patient by an equation known in the art or the like. For example, according to Dietary Reference Intakes for Japanese (2015) published by the Ministry of Health, Labour and Welfare, the rate is 21.5 kcal/kg body weight/day for males who are 50 years old or older and 21.5 kcal/kg body weight/day for females who are 50 years old or older, but is 24.0 kcal/kg body weight/day for males who are 18 to 29 years old and 22.1 kcal/kg body weight/day for females who are 18 to 29 years old.

As a specific embodiment, an example of a modified Atkins method comprises, for example, the following steps.

1) a step of feeding diet, for about the first week (period can be appropriately extended or shortened, which may be several days to several weeks), at calorie of about kcal/kg body weight based on real a body weight, no restriction on fat, no restriction on protein, and about 10 g or less of carbohydrate, and preferably a daily calorie of about 1500 kcal based on a real body weight of 50 kg and a ratio of about 140 g of lipid:about 60 g of protein:about 10 g of carbohydrate (ketogenic ratio (lipid/(protein+carbohydrate)) is about 2:about 1), while other nutrients can be ingested without restriction and required trace amounts of elements or vitamins are appropriately ingested using a supplement or the like;

2) providing diet for about the second week to about the third month (the period may be appropriately extended or shortened and shifted ahead or behind of 2 weeks, and the third month may also be slightly shifted ahead or behind (about 1, 2 or several weeks of shift is acceptable)), preferably with an MCT oil or ketogenic formula, by giving guidance while referring to the blood ketone body value so that acetoacetic acid is not about 500 μmol/L or greater and 3-hydroxybutyrate is not about 1000 μmol/L or less, with a goal of, if possible, acetoacetic acid of about 1000 μmol/L or greater and β-hydroxybutyrate of about 2000 μmol/L or grater, wherein the goal is daily intake of carbohydrate of about 20 g or less, daily calorie of about 1400 to about 1600 kcal, a ratio of about 120 to about 140 g of lipid:about 70 g of protein:about 20 g of carbohydrate, and a ketogenic ratio of about 2:1 to about 1:1; and 3) after the third month (the end of period of 2) itself would shift when the third month shifts), providing a single intake of carbohydrate of about 10 g/day and daily intake of about 30 g or less, and providing the diet in accordance with 2) with respect to others.

As used herein, "X to Y" indicating a range refers to "X or greater and Y or less". Further, "about" indicates the significant figures, unless specifically noted otherwise. Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described hereinafter based on Examples. The aforementioned description and the following Examples are not provided to limit the present invention, but for the sole purpose of exemplification. Thus, the scope of the present invention is not limited to the embodiments and Examples specifically described herein and is limited only by the scope of claims.

EXAMPLES

Examples of the present invention are disclosed hereinafter. Clinical trials have been conducted in compliance with the Declaration of Helsinki and the standards of the Osaka University, and non-clinical trials were conducted in compliance with the standards set forth at the research lab of Meiji Co., Ltd., based on the spirit of animal welfare.

Example 1

The usefulness of ketogenic formula on cancer was evaluated with a colon-26 cell transplanted cancer bearing model using mice.

(Materials and Methods)

Colon-26 cells ($5×10^5$ cells) of a colon cancer cell line were subcutaneously transplanted under the armpit in 30 seven week old male CDF1 mice. After transplantation, the mice were separated into a control group of 10 mice and KF group (ketogenic formula group) of 10 mice. The control group was given formulated animal feed AIN-93G and the KF group was given a ketogenic formula for 21 days after colon-26 cell transplantation. 817-B provided by Meiji Co., Ltd. was used as the ketogenic formula. The composition of the ketogenic formula (817-B) is shown in the following Table 2A. The energy balance of main ingredients of each sample is shown in Table 2B.

TABLE 2A

| | |
|---|---|
| Manufacturer name | Meiji |
| Product model number | 817-B |
| Can content (g) | 250 |
| Standard composition | in 100 g of product |
| Protein (g) | 15.0* |
| Lipid (g) | 71.8** |
| Carbohydrate (g) | 8.8*** |
| Ash (g) | 2.4 |
| Moisture (g) | 2.0 |
| Energy (kcal) | 741 |
| Vitamin A (μgRE) | 600 |
| Vitamin $B_1$ (mg) | 0.6 |
| Vitamin $B_2$ (mg) | 0.9 |
| Vitamin $B_6$ (mg) | 0.3 |
| Vitamin $B_{12}$ (μg) | 4 |
| vitamin C (mg) | 50 |
| Vitamin D (μg) | 12.5 |
| Vitamin E (mgα-TB) | 6 |
| Vitamin K (μg) | 30 |
| Pantothenic acid (mg) | 2 |
| Niacin (mg) | 6 |
| Folic acid (mg) | 0.02 |
| Calcium (mg) | 350 |
| Magnesium (mg) | 36 |
| Sodium (mg) | 165 |
| Potassium (mg) | 470 |
| Phosphorous (mg) | 240 |
| Chlorine (mg) | 320 |
| Iron (mg) | 6 |
| Copper (μg) | 350 |
| Zinc (mg) | 2.6 |
| Standard milk formulation concentration (W/V %) | 14% |
| Osmotic pressure of milk formulation (mOsm/kg · $H_2O$) | 92 |

Remarks
*Milk protein
**Required fatty acid adjusted fat 32.1 MCT oil 39.7
***Milk sugar
oKetogenic ratio 2.9

TABLE 2B

| Feed composition (energy balance) | | |
|---|---|---|
| | AIN-93G | Ketogenic formula |
| [Energy ratio] | | |
| Protein (% E) | 20.2 | 8.1 |
| Lipid (% E) | 15.9 | 87.2 |
| Long chain fatty acid oil and fat (% E) | 15.9 | 39.0 |
| Medium chain fatty acid oil and fat (% E) | 0.0 | 48.2 |
| Available carbohydrate (% E) | 63.9 | 4.7 |
| [Main ingredients] | | |
| Protein | Milk protein | Milk protein |
| Lipid | Long chain fatty acid oil and fat | Long chain fatty acid oil and fat Medium chain fatty acid oil and fat |
| Available carbohydrate | Corn starch Saccharose | Milk sugar |

% E: % energy

Results

Figure 2:
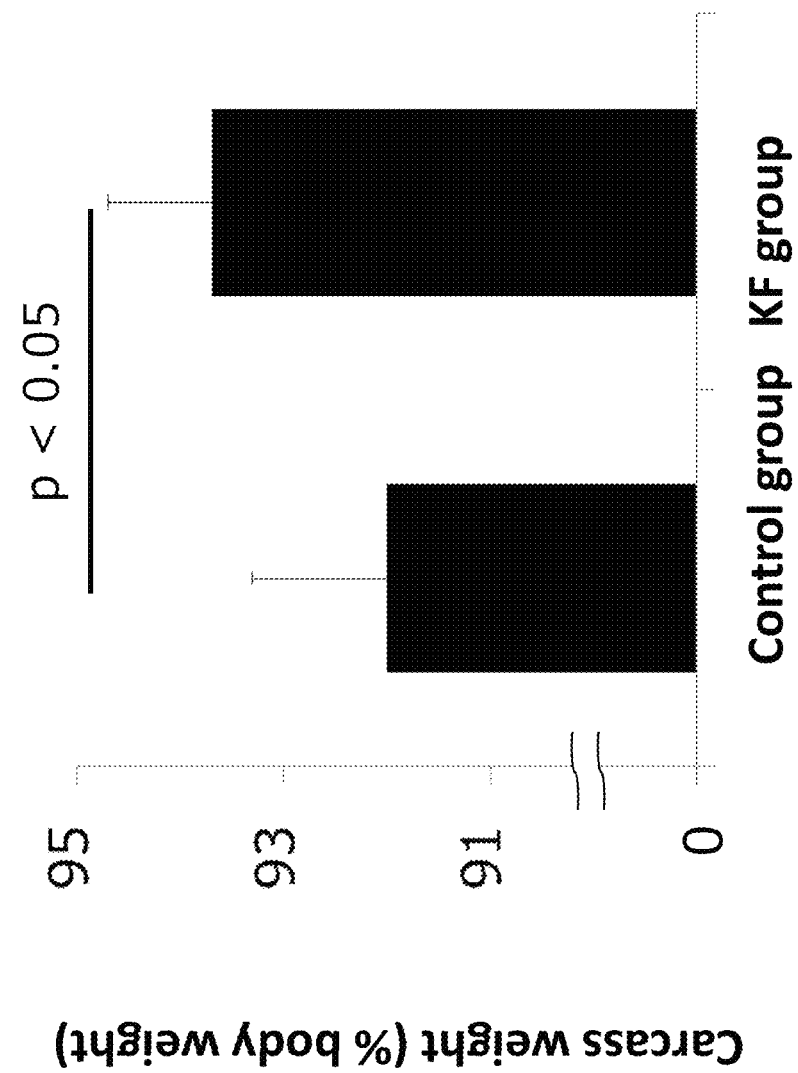
FIG. 2 shows the body weight excluding tumor on day 21 after tumor transplant in the control group and the KF group.
Figure 3:
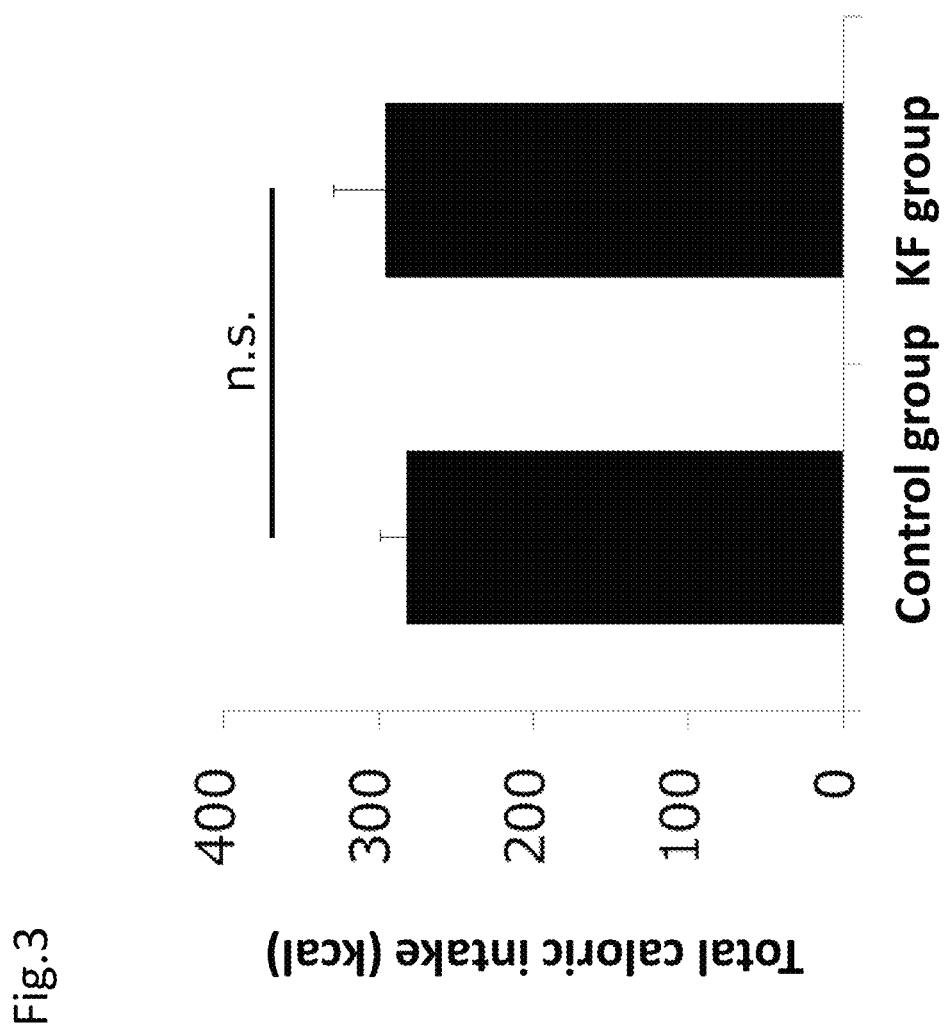
FIG. 3 shows data for total caloric intake in the control group and the KF group.
Figure 4:
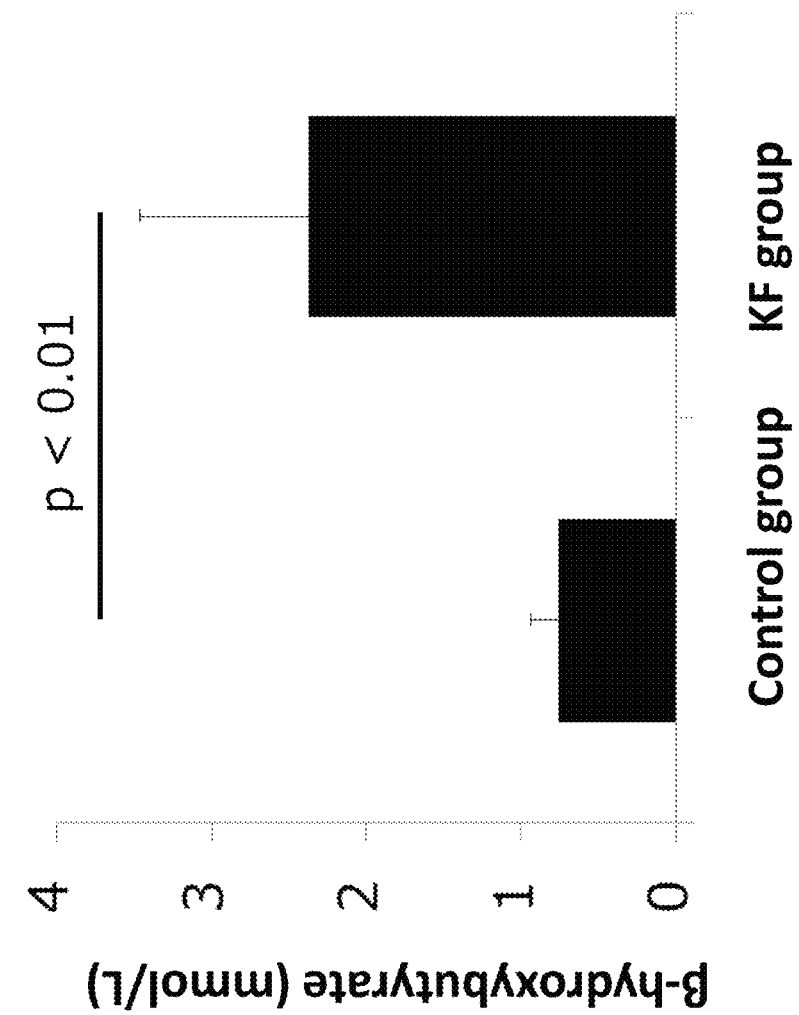
FIG. 4 shows data for blood β-hydroxybutyrate on day 21 after tumor transplantation in the control group and the KF group.
Figure 5:
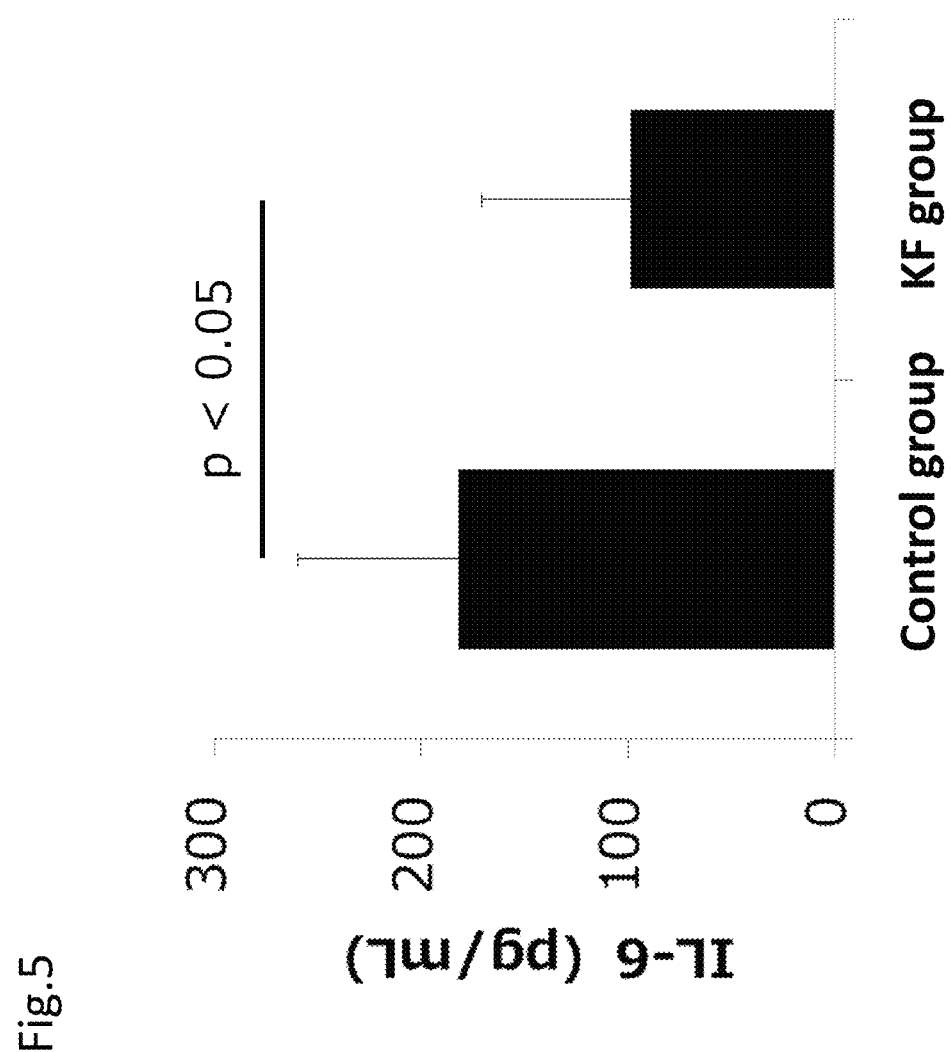
FIG. 5 shows data for blood IL-6 concentration on day 21 after tumor transplantation in the control group and the KF group.

The tumor weight on day 21 after colon-26 cell transplantation was 1.69±0.25 g in the control group, while the tumor weight in the KF group was 1.33±0.16 g, which was significantly reduced relative to the control group (p<0.01) (FIG. 1). Further, carcass body weight, which excludes the tumor weight from the body weight, of the KF group was significantly higher relative to the control group (FIG. 2). Further, it is generally known that energy intake decreases when ketogenic diet (available carbohydrate restricted high fat diet) is given to animals. Meanwhile in the present Example, there is no difference in the total caloric intake of the KF group relative to that of the control group, thus maintaining the caloric intake (FIG. 3). The blood ketone body concentration in the KF group was significantly higher relative to that in the control group (FIG. 4). Furthermore, it, was elucidated that the blood inflammatory cytokine (IL-6) concentration is significantly suppressed in the KF group relative to that in the control group (FIG. 5). In view of the above, it was found that a ketogenic formula effectively increases the blood ketone body concentration, suppresses inflammatory cytokines, and reduces tumor without reducing total energy intake or carcass body weight.

Example 2

Figure 6:
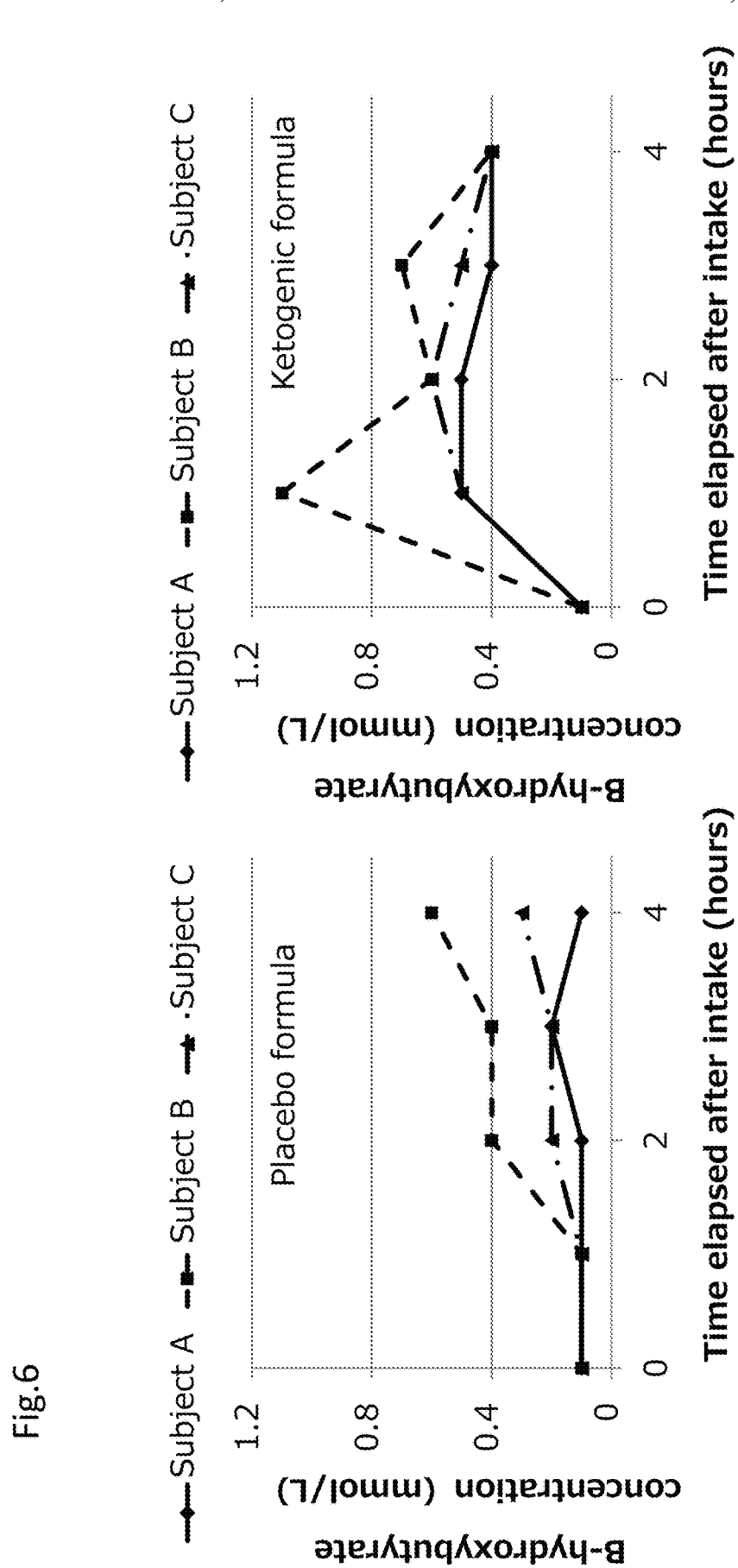
FIG. 6 shows data for blood β-hydroxybutyrate concentration in healthy adults. The left graph shows the blood β-hydroxybutyrate concentration when a placebo formula (composition with the same composition as a ketogenic formula, with all lipids being long chain fatty acid oil and fat (free of medium chain fatty acid oil)) was ingested, and the right graph shows the blood β-hydroxybutyrate when a ketogenic formula was ingested. The horizontal axis of each graph indicates the time elapsed after intake (hours).

The effect of increase in ketone bodies by medium chain fatty acid oil and fat was studied. Three healthy adults were asked to ingest a ketogenic formula or a placebo formula (composition with the same composition as a ketogenic formula, having lipids that are all long chain fatty acid oil and fat (free of medium chain fatty acid oil and fat)), and the blood ketone body concentration after intake was measured. A greater increase in the blood ketone body concentration was confirmed with the ketogenic formula relative to the placebo formula (FIG. 6). It was found that a ketogenic formula increases particularly the ketone bodies among ketogenic diet in not only animals but also humans. Further, it is understood that use of medium chain fatty acid as lipids is desirable for attaining an effect of increasing ketone bodies.

In this Example, a single center open trial was conducted with 5 patients. Target patients were selected under the following criteria.

(Compatibility Criteria)

Target patients are those with non-small cell pulmonary malignant which has been pathologically diagnosed by specimen resection or biopsy at Stage IV and PS2 or lower.

Patients and their family members have agreed to continue dietary therapy.

(Exclusion Criteria)

Cancer patients who are incapable of oral ingestion or cancer patients having a PS or 3 or higher Patients with a diabetes complication (Endpoints)

Selected patients were evaluated with respect to the following endpoints.

TABLE 3

|  | Before therapy | After 1 month | After 2 months | After 3 months | After 12 months |
|---|---|---|---|---|---|
| Ketogenic diet guidance/continuation rate | • | • | • | • | • |
| QOL score of cancer therapy | • | • | • | • | • |
| Gastrointestinal symptom score | • | • | • | • | • |
| Blood/urine test | • |  |  | • | • |
| PET-CT | • |  |  | • | • |
| mRNA collection | • |  |  | • | • |

The endpoints are explained below.

(1) Ketogenic diet: evaluation of guidance for low carbohydrate high fat diet and continuation rate (2) Change in QOL score of cancer therapy: EORTCQLQ-C30

(3) Change in gastrointestinal symptom score: GSRS (4) Change in clinical test values: the following were measure:

Various Tumor Markers

General biochemistry (hs-CRP, T.G., T.Chol, LDL-C, HDL-C, TP, ALB, Cr, BUN, AST, ALT, ALP, γ-GTP, blood sugar, IRI, HbA1c)

Blood Ketone Body Fraction

WBC fraction, Hb, Ht, platelet count

Inflammatory cytokines (IL-6 and TNF-α)

(5) Image evaluation by PET-CT before and after introduction of ketogenic diet (6) Comprehensive analysis of mRNA derived from peripheral blood mononuclear cell with a next generation sequencer (for example, commercially available sequencer such as Roche 454 or Illumina is used) (discussed in detail in Example 3)

(Introduction of Ketogenic Diet)

Guidance was provided for modified Atkins diet as the ketogenic diet. The details are as follows.

1) for the first week, the goal was calorie of 30 kcal/kg based on the real body weight, no restriction on lipids, no restriction on protein, and 10 g or less of carbohydrate. Specifically, for the early stages of introduction, daily calorie was 1500 kcal based on a real body weight of 50 kg and the ratio was 140 g of lipids:60 g of protein:10 g of carbohydrate.

The target ketogenic ratio (lipid/(protein+carbohydrate)) was 2:1. Other nutrients could be ingested without restriction. Required trace amounts of elements or vitamins were appropriately ingested using a supplement or the like. Diet was initially prepared in line with a menu created by a nutritional management team.

2) for the second week to the third month, while referring to the blood ketone body value, the goal was daily intake of carbohydrate of 20 g or less, daily calorie of 1400 to 1600 kcal, a ratio of 120 to 140 g of lipid:70 g of protein:20 g of carbohydrate, and a ketogenic ratio of 2:1 to 1:1. MCT oil (Nissin Oillio) or ketogenic formula (Meiji) was used for supplementing calories.

3) After the third month, a single intake of carbohydrate was 10 g/day and daily intake was 30 g or less, and others were in accordance with 2).

Upon introduction, explanation was provided that a temporary hypoglycemia, nausea, fatigue, or the like would appear. Actual nutritional guidance was rendered under the guidance of a nutritionist. Patients for whom the diet was prepared were present for the nutritional guidance.

Ketogenic diet (75 to 80% lipid) has been administered for an extended period of time to child epileptic patients, so that the safety thereof has been confirmed. Thus, the diet is described in the 2010 edition of the COCHRANE LIBRARY. The document was also referred to as a reference for the actual policy. While nausea, fatigue, hypoglycemia, or the like may be temporary observed in the early stages of introduction, it has been confirmed that they can be sufficiently handled. Since this is a high lipid diet, there is a possibility that a certain percentage of patients cannot continue the ketogenic diet due to their preference. Such issues can be handled by cooperation with the nutrition management team.

(Patients)

There were actually 5 patients who were subjected to the diet. The patients are summarized with the endpoints in the following Table. The number of days of survival is the number of days as of Aug. 31, 2015 for the surviving cases.

TABLE 5

| Case | Previous chemotherapy | History of radiation therapy | History of surgery |
|---|---|---|---|
| 1 | CBDCA + PEM + BEV (6 courses) PEM + BEV (4 courses) | None | None |
| 2 | None | None | None |
| 3 | CDDP + PEM PEM DCC | None | None |
| 4 | Erlotinib | γ knife 2013 | Left lower lobe resection 2011 Left temporal lobe tumor extraction 2013 |
| 5 | CBD + PAC (3 sessions) PEM (2 sessions) Iressa CBDCA + PAC + BEV (5 sessions) | Right vertebral body rib 60 Gy 2014 | Right upper lobe resection 2010 |

TABLE 4

| Continuation | Therapy assessment | Date of onset | Date of IC | Date of outcome | # of days of survival |
|---|---|---|---|---|---|
| 3 months | CR | Jun. 28, 2012 | Feb. 27, 2013 | Aug. 31, 2015 | 915 |
| Withdrew consent | death | Dec. 6, 2012 | Jul. 1, 2013 | Feb. 23, 2015 | 602 |
| Continuation | PD | Jun. 27, 2011 | Aug. 28, 2013 | Aug. 31, 2015 | 773 |
| Continuation | CR | Oct. 18, 2011 | Feb. 19, 2014 | Aug. 31, 2015 | 558 |
| Discontinued participation | death | Aug. 17, 2010 | Jun. 18, 2014 | Dec. 7, 2014 | 172 |

| Case | Sex | Age | Height (cm) | BMI | Disease | STAGE | TNM classification | Tissue |
|---|---|---|---|---|---|---|---|---|
| 1 | F | 56 | 159 | 19.7 | Pulmonary adenocarcinoma | IV | cT2aN0M1a | adeno carcinoma |
| 2 | F | 73 | 154.2 | 20.6 | Pulmonary adenocarcinoma | IV | cT4N0M1a | adeno carcinoma |
| 3 | M | 65 | 174 | 22.5 | Pulmonary adenocarcinoma | IV | No explicit description in medical record | adeno carcinoma |
| 4 | F | 53 | 151 | 19.4 | Pulmonary adenocarcinoma | IV | pT2aN0M0 | adeno carcinoma |
| 5 | M | 45 | 169 | 22.4 | Pulmonary adenocarcinoma | IV | t1BN0M0 t3M0N1a | adeno carcinoma |

Figure 7:
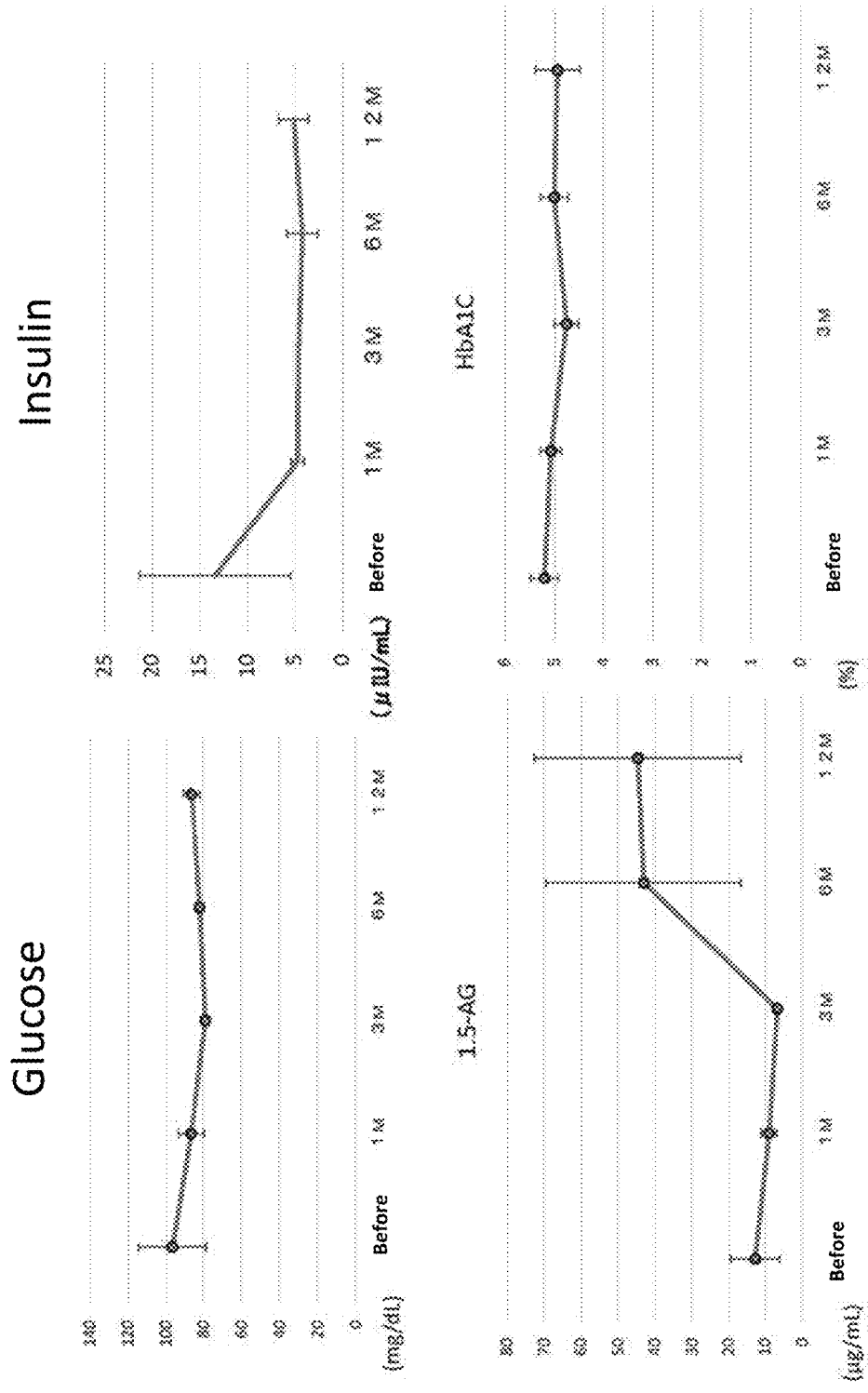
FIG. 7 shows blood data for 3 cases with continued ketogenic diet. The time elapsed (up to 12 months) is shown in the top row for, from the left, glucose and insulin, and in the bottom row for, from the left, 1,5-anhydro-D-glucitol (1,5-AG) and HbA1C. Each graph shows error bars and the unit.
Figure 8:
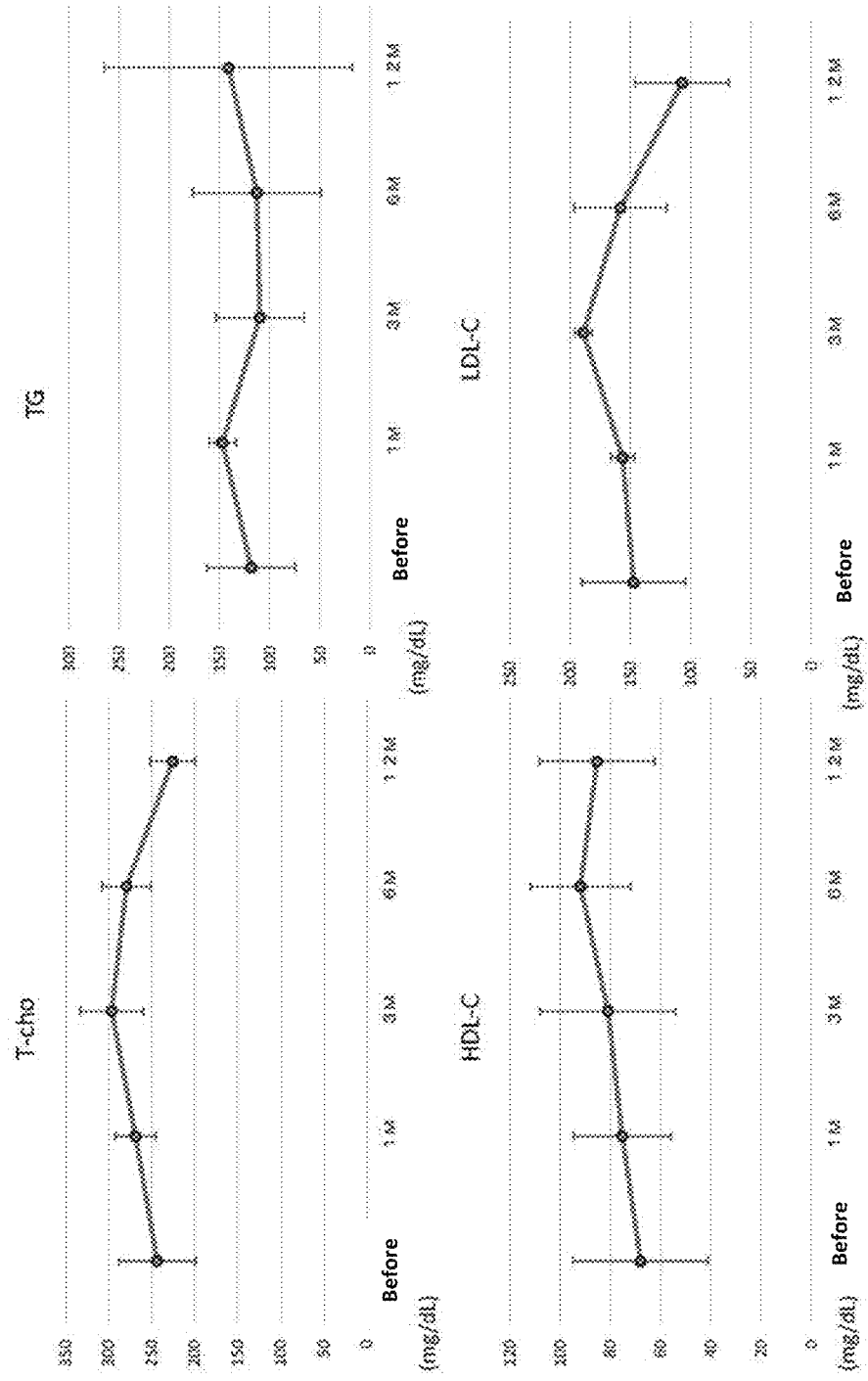
FIG. 8 shows blood data for 3 cases with continued ketogenic diet. The Figure shows, from the top left, total cholesterol (T-cho) and triglyceride (TG) and, from the bottom left, HDL cholesterol (HDL-C) and LDL cholesterol (LDL-C) HDL-C. Each graph shows error bars and the unit.
Figure 10:
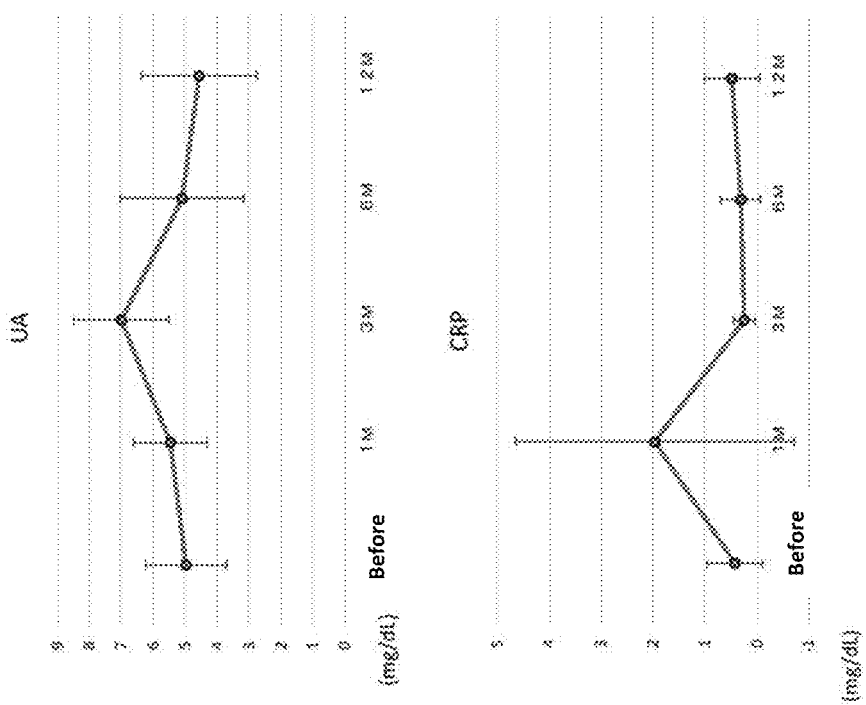
FIG. 10 shows blood data for 3 cases with continued ketogenic diet. The top row shows uric acid (UA) and the bottom row shows C-reactive protein (CRP). Each graph shows error bars and the unit.

The following Table shows records of therapy other than ketogenic diet therapy in each case. The blood data of 3 cases (cases 1, 3, and 4) of this Example is shown in FIGS. 7 to 10. FIG. 7 shows the time elapsed (up to 12 months) for glucose, insulin, 1,5-anhydro-D-glucitol (1,5-AG), and HbA1C. FIG. 8 shows total cholesterol (T-cho) and triglyceride (TG) and, from the bottom left, HDL cholesterol (HDL-C) and LDL cholesterol (LDL-C) HDL-C. FIG. 9 shows venous blood acetoacetic acid and the bottom row shows venous blood β-H butyrate. FIG. 10 shows uric acid (UA) and the bottom row shows C-reactive protein (CRP).

As shown in the above therapeutic assessment, remission was reached in two patients (CR=Complete Response) and significant healing was observed in 1 patient (PD=Progressive Disease) in consented cases 1, 3, and 4.

Each case is disclosed in detail below.

(Case 1)

Case: 56 years old female, diagnosis of pulmonary adenocarcinoma (stage IV)

Current clinical history: the patient consulted a physician in June 2012, and was diagnosed as pulmonary adenocarcinoma (stage IV, EGFR mutation positive). The patient started anticancer agent therapy from the end of July 2012.

(Therapeutic Progress Prior to Starting Diet Therapy of the Invention)

From July to November of 2012, 6 courses of carboplatin+pemetrexed+bevacizumab were administered, and pleural effusion was improved.

From December 2012 to February 2013, 4 courses of pemetrexed+bevacizumab were administered.

From early 2013, increase in CEA was observed. The patient requested cancer supportive care, and started cancer supportive care with the ketogenic diet of the invention from Mar. 4, 2013.

On Jun. 13, 2013, head MRI found brain metastasis (5 mm), which was eliminated with γ-knife. There is currently no recurrence thereof.

Tarceva administration was started at the same time.

The hospital discontinued ketogenic diet intervention.

On Aug. 8, 2013, ninjin-yoei-to was prescribed.

On Oct. 3, 2013, Metgluco (metformin hydrochloride) was prescribed.

In January 2014, surgery was performed on the primary lesion in the lung.

In April 2014, ninjin-yoei-to/Crestor (rosuvastatin)/Lotriga (omega-3-acid ethyl ester) were prescribed, and currently under follow-up observation.

At the end of May 2014, the patient received diagnosis after 1 year of ketogenic diet intervention.

It is reported that the patient is still able to work, with no change in body weight at around 45 kg, and as for the diet, the patient has held back on available carbohydrate for dinner and is mindful of taking oil such as olive oil or coconut oil. It was determined that the dietary therapy of the invention is being continued from the result of an interview.

(Case 2)

Case: 73 years old female, diagnosis of pulmonary adenocarcinoma (stage IV)

(Therapeutic Progress)

In November 2012, interstitial pneumonia/multiple pulmonary nodule were found by chest CT, so that the patient was suspected of having primary lung cancer.

In December 2012, the patient was under follow-up observation with prednisolone 5 mg and salazosulfapyridine (Azulfidine) 500 mg.

In March 2013, there was no change in interstitial pneumonia/collagen disease of lung/left lung apex nodule, and the nodule at left lung S10 slightly increased in the chest CT.

In April 2013, the patient was hospitalized for bronchoscope, and curetting was performed three times in the left B1+2b. The patient was diagnosed with pulmonary adenocarcinoma.

In May 2013, PET-CT found accumulation in the left lung/rectum/cervical vertebra. The patient was hospitalized for left S10CTGB. L858R mutation was positive in an EGFR mutation test.

In September 2013, the patient considered cancer supportive care using the ketogenic diet of the invention, but withdrew the consent.

In September 11, the patient started oral dosing of gefitinib (Iressa) 250 g.

In May 2014, oral dosing was continued because side effects of Iressa were not found.

In June 2014, the patient was hospitalized for controlling effusion.

In August 2014, the patient was hospitalized. The body weight decreased 8 kg (50 kg→42 kg) and to 41 kg in October 2014

On Feb. 23, 2015, the patient passed away.

(Case 3)

Case: 65 years old male, diagnosis of left upper lobe primary pulmonary adenocarcinoma (pleural dissemination stage IV)

(Therapeutic Progress)

On Jun. 27, 2011, pleural dissemination was found by thoracotomy, so that chemotherapy was introduced.

In August 2011, cisplatin+pemetrexed (Alimta) was introduced, then 20 courses of maintenance therapy were administered with pemetrexed alone In February 2013, docetaxel (Taxotere) therapy was started due to an increase in CEA and pleural dissemination.

On Sep. 4, 2013, the ketogenic diet of the invention was started.

In November 2013, peripheral nervous disorder manifested, so that anticancer agent administration was discontinued.

In December 2013, metformin and ninjin-yoei-to were additionally prescribed.

In March 2014, the patient was diagnosed with carcinomatous pleurisy. Rosuvastatin/pioglitazone/EPA formulation was additionally prescribed.

In June 2014, ninjin-yoei-to dosage was increased, rosuvastatin was temporarily discontinued, and oral administration of amlodipine 5 mg was started.

In July 2014, a fourth course of paclitaxel+carboplatin+bevacizumab was administered.

In August 2014, the patient was released from the hospital.

In September 2014, single agent therapy of bevacizumab was administered.

In October 2014, single agent therapy of Avastin was administered, and ketogenic diet restricted available carbohydrate to 30 g.

In November 2014, single agent therapy of bevacizumab was administered.

In December 2014, CEA results stabilized, so that bevacizumab administration, and olive oil, MCT oil, and ketogenic diet were continued.

In January 2015, bevacizumab administration was discontinued. The patient was under follow-up observation with carvedilol (Artist) 2.5 mg, aspirin 100 mg, and Nitrol R 20 mg.

In February 2015, the patient was hospitalized. TS-1 was started.

In June 2015, vinorelbine (Navelbine) administration was started, but discontinued on Jun. 22, 2015.

On Jul. 24, 2015, gemcitabine (Gemzar) administration was started. Thermotherapy was administered 8 times.

On Sep. 29, 2015, gemcitabine administration was completed after the fourth administration.

In November 2015, bone scintigraphy revealed metastasis to 7 sites. Anti-RANKL antibody (Ranmark) administration was started. Brain MRI found brain metastasis. γ knife was not used.

On Nov. 17, 2015, once every morning erlotinib (Tarceva) 150 mg administration was started.

On Jan. 7, 2016, nivolumab (Opdivo) administration was started, for a total of 4 administrations.

On Mar. 11, 2016, the patient was diagnosed with cerebral infarction by brain MRI, exhibiting symptoms such as the inability to articulate speech.

In April 2016, the patient had mesentery metastasis and was in a fasting state.

On May 3, 2016, the patient passed away.

(Case 4)

Case: 52 years old female, diagnosis of non-small cell lung cancer (stage IV)

(Therapeutic Progress)

In July 2011, abnormal shadow in the chest area was noted. Left lower lobe resection was performed on Oct. 18, 2011 due to lung cancer. The patient was diagnosed with non-small cell lung cancer (adenocarcinoma, pT2aNOMO, pStage IB).

In December 2011, oral administration of UFT400 was started.

In July 2013, a 7 cm lump was found in the left temporal lobe. Left temporal lobe lump extraction surgery was performed. The patient was diagnosed with adenocarcinoma.

In September 2013, EGFR mutation was found. Oral administration of erlotinib (Tarceva) 100 mg was started.

Local recurrence was found in head MRI. γ-knife was performed at Shiroyama Hospital.

In February 2014, the ketogenic diet therapy of the invention was started.

In March 2014, the uric acid value suddenly increased. Allopurinol (Zyloric) was prescribed.

In May 2014, abnormal accumulation suggesting recurrence/metastasis was not found in PET-CT or evaluation after 3 months of ketogenic diet intervention. Since the cholesterol level was high, rosuvastatin (Crestor) was additionally prescribed.

In July 2014 (after 4 months of ketogenic diet intervention), no problem in metabolic system data at available carbohydrate restricted to 30 g. Allopurinol and rosuvastatin administration was continued.

In August 2014 (after 5 months of ketogenic diet intervention, available carbohydrate was restricted to 30 g, allopurinol was changed to febuxostat, and eczema due to erlotinib was found on the head.

In October 2014 (after 7 months of ketogenic diet intervention), available carbohydrate was restricted to 30 g, and febuxostat administration was continued.

In February 2015 (after 1 year of ketogenic diet intervention), available carbohydrate was restricted to 30 g, and abnormal accumulation suggesting recurrence/metastasis was not found in PET-CT.

In February 2016 (after 2 years of ketogenic diet intervention), available carbohydrate was restricted to 30 g, and slight increasing trend of lymph accumulation at the left lung was found in PET-CT.

In April 2016 (after 2 years and 2 months of ketogenic diet intervention), available carbohydrate was restricted to 30 g, and erlotinib was prescribed.

In June 2016 (after 2 years and 4 months of ketogenic diet intervention), available carbohydrate was restricted to 30 g, and erlotinib was prescribed.

In August 2016 (after 2 years and 6 months of ketogenic diet intervention), available carbohydrate was restricted to 30 g, and erlotinib was prescribed.

(Case 5)

Case: 46 years old male, diagnosis of non-small cell lung cancer (adenocarcinoma stage IV)

(Therapeutic Progress)

In June 2010, a shade of a lump was noticed in the right upper lung field. The patient was diagnosed with lung cancer (adenocarcinoma, right S1 primary, T1bNOMO, stage Ib). Upper lobe resection was performed on Aug. 17, 2010 (ND2a, T3NOM1a, stage IV (pleural dissemination and intrapulmonary metastasis at the lung apex)).

In September 2010, 3 courses of CBDCA+PAC were administered. CEA decreased to 3.0. The administration was temporarily suspended.

In July 2011, multiple instances of several mm intrapulmonary metastasis was found by chest CT In September 2011, 2 courses of single agent of PEM were administered.

In May 2012, gefitinib (Iressa) administration was started.

In September 2012, Hasumi vaccine was concomitantly used.

In August 2013, CEA reached 150. Loculated pleural effusion was found by PET-CT. The rib, left cervical lymph node metastasis was found.

In October 2013, gefitinib and Hasumi vaccine administration terminated.

From October 2013 to February 2014, 5 courses of CBDCA 500 mg+PAC 300 mg+Bev 1000 mg were administered.

From Mar. 14 to Apr. 26, 2014, radiation irradiation was started on the soft tissue around the rib joints and right upper vertebra and completed at a total of 60 Gy.

In July 2014, ketogenic dietary therapy was scheduled, but the intervention was temporarily suspended due to gastric discomfort, vomiting and the like.

On Dec. 7, 2014, the patient has passed away.

(Results)

Figure 12:
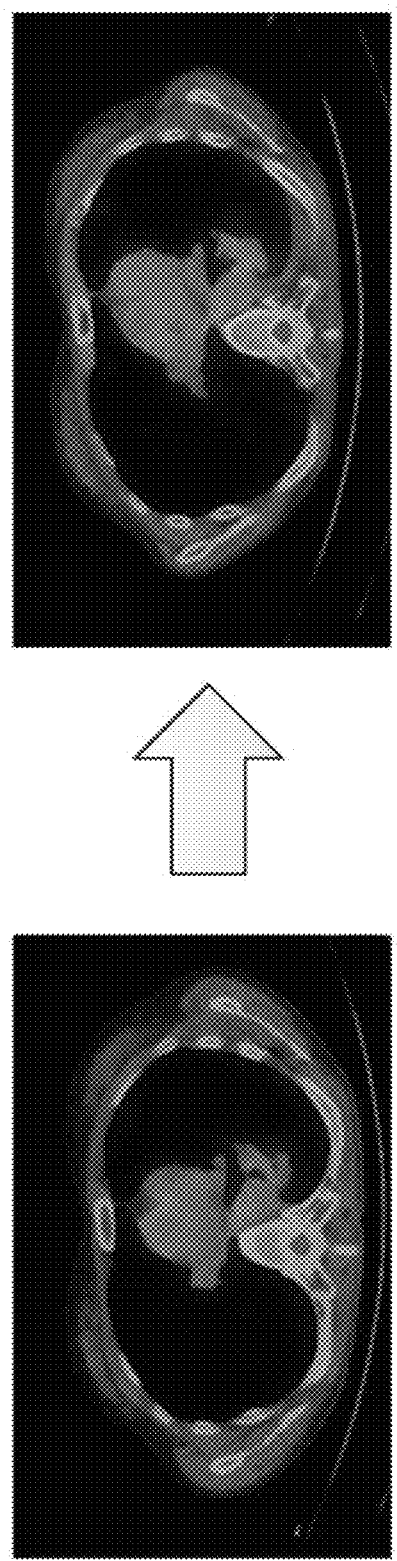
FIG. 12 shows a comparison of PEG-CT in one case before and after therapy (after 3 months). According to radiological interpretation, the known lump toward the center of the left lung S6 appeared to have slightly contracted, while the activity is determined to be sustained with FDG accumulation (SUVmax: previously 2.4→ currently 2.8). Further, left pleural effusion and FDG accumulation are enhanced in a wide range in the left pleura and interlober pleura. It can be seen that a nodule found in contact with the interlober pleura has slightly expanded, accompanying FDG accumulation.

The clinical trial was started in January 2013. Informed consent was obtained from 5 patients by March 2015. Two males and three females had an average age of 58.4±10.1, height of 161.4±9.7 cm, body weight of 55.1±10.4 kg, and EMI of 20.9±1.5. In all cases, the patients had stage IV pulmonary adenocarcinoma. 4 patients had history of chemotherapy and 2 patients had a history of radiation therapy. One patient withdrew the consent. Ketogenic diet was introduced to 3 patients, but not to one patient due to stomach discomfort. In addition to diet guidance, MCT oil or ketogenic formula was used. As a result, for blood ketone bodies, acetoacetic acid increased to 986.6±453.3 μmol/L and β-H butyrate increased to 2298±1270.4 μmol/L in one month. In addition, the expected hypoglycemia, nausea, fatigue or the like was not observed, and improving trend was exhibited in systemic condition scale of 11.7±9.6-4 61.1±9.6 and GSRS score of 1.64±0.42 1.24±0.15 in 3 months. PET-CT after 3 months found partial contraction in one patient, but found no change in two patients (FIG. 12). For one patient, cranial metastasis was found so the patient left the ketogenic diet after the 3 month evaluation, but elimination of tumor was found with γ-knife procedure, contraction of the primary lesion was observed with erlotinib administration, and CR was reached with surgery. For one patient, erlotinib was continuously administered, and one patient concurrently used multiple chemotherapies. Three patients were alive as of the priority date. As of the filing date, two patients were alive. However, two patients who did not receive the dietary therapy of the invention unfortunately could not survive.

Other blood indicators (glucose, insulin, 1,5-anhydro-D-glucitol (1,5-AG), HbA1C, total cholesterol (T-cho) and triglyceride (TG) and, from the bottom left, HDL cholesterol (HDL-C) and LDL cholesterol (LDL-C) HDL-C, uric acid (UA) and C-reactive protein (CRP)) were stable without irregularity that would be especially problematic during the practice of ketogenic diet (FIGS. 7 to 10).

As of Sep. 1, 2016, two patients who exhibited remission (CR) are still alive, surviving 1282 days (case 1) and 925 days (case 4) from the date of consent (Table 6). One patient with PD has passed away, but life was prolonged for 979 days from the date of consent. The three year survival rate of stage IV non-small cell lung cancer patients who have received chemotherapy at the National Cancer Center Hospital East, from the survival curve from 2002 to 2006 (569 patients), was 11% (http://www.ncc.go.jp/jp/about/disclosere/result_e.html#05). In view of the above, the results in the present Example can be concluded as ketogenic diet drastically improving life prognosis of non-small cell lung cancer patients.

TABLE 6

| | | | | Body | | | | # of |
| | | | Height | weight | | | Therapeutic | Date of | days of |
| Case | Sex | Age | (cm) | (kg) | BMI | Disease | effect | outcome | survival |
|---|---|---|---|---|---|---|---|---|---|
| 1 | F | 56 | 159 | 49.8 | 19.7 | Pulmonary adenocarcinoma | CR | Sep. 1, 2016 | 1282 |
| 2 | F | 73 | 154.2 | 49.1 | 20.6 | Pulmonary adenocarcinoma | death | Feb. 23, 2015 | 602 |
| 3 | M | 65 | 174 | 68.2 | 22.5 | Left upper lobe primary pulmonary adenocarcinoma | death | May 3, 2016 | 979 |
| 4 | F | 53 | 151 | 44.3 | 19.4 | Pulmonary adenocarcinoma | CR | Sep. 1, 2016 | 925 |
| 5 | M | 45 | 169 | 64 | 22.4 | Non-small cell lung cancer | death | Dec. 7, 2014 | 172 |

↓Age and number of days of survival as of the date of consent are as of, when alive, Sep. 1, 2016

Pictures of PET-CT before and after the therapy of the invention for case 1 are shown in FIG. 12. From radiological interpretation, an about 3 cm lump with irregular peripheral edges was found toward the center of left lung S6, but it appears that the known lump toward the center of left lung S6 had shrunk after the therapy. In addition, it is determined that activity is sustained with respect to FDG accumulation (SUVmax: previously 2.4→currently 2.8). Further, left pleural effusion and FDG accumulation are enhanced in a wide range in the left pleura and interlober pleura. It can be seen that a nodule found in contact with the interlober pleura has slightly expanded, accompanying FDG accumulation.

(Discussion)

In view of the above results in Example 2, three patients who received the dietary therapy of the invention exhibited remission or significant healing, while the two patients who did not receive the dietary therapy of the invention unfortunately were unable to survive. Thus, the dietary therapy of the invention can be understood as having a significant effect on cancer and significantly improved QOL, relative to a similar control. Existing cancer therapies are surgical resection, chemotherapy, and radiation therapy. The therapeutic effect by chemotherapy is not considered sufficient for lung cancer, pancreatic cancer and the like. Since ketogenic diet was demonstrated to have the potential to improve life prognosis against such advanced cancer, it is considered possible to develop a dietary therapy that is effective for cancer patients.

(Evaluation by Kaplan-Meier Method)

Figure 11:
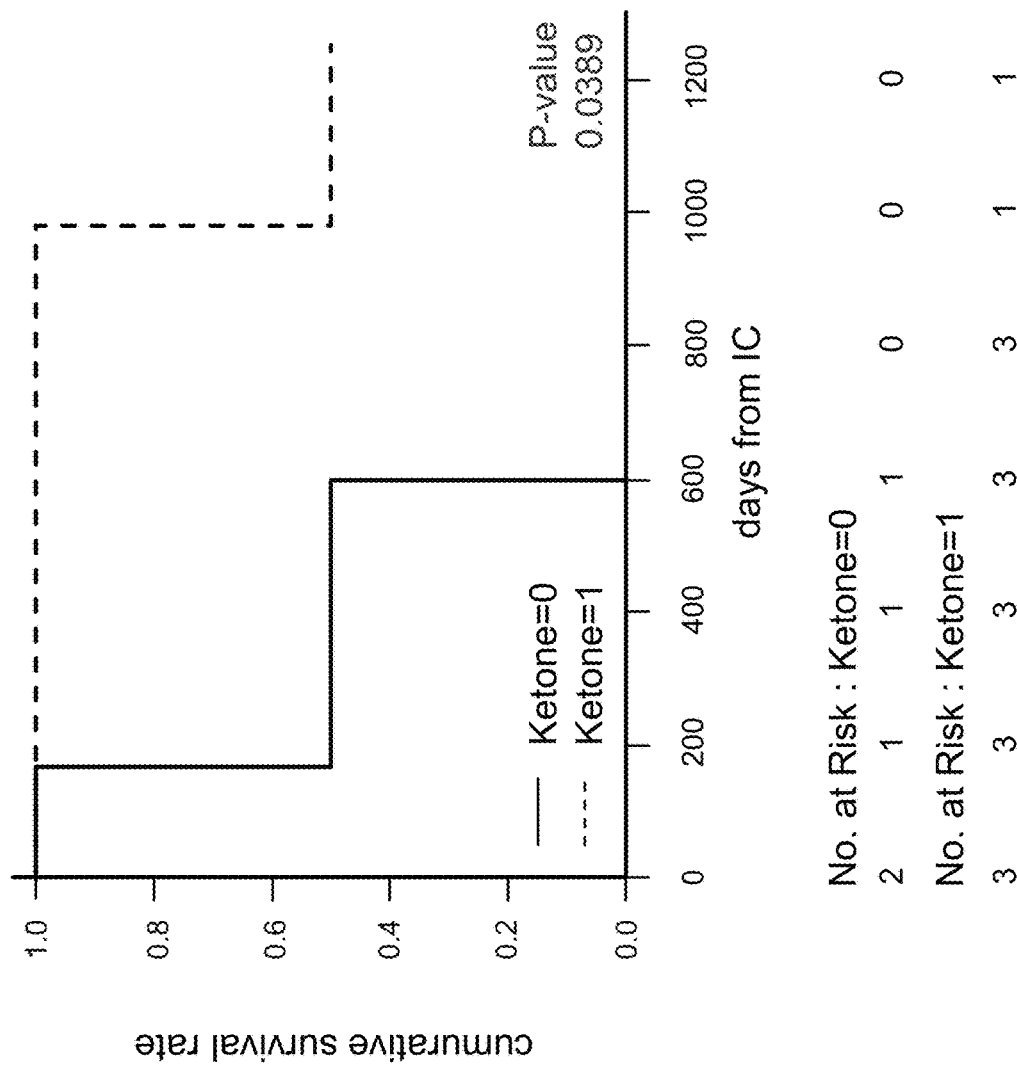
FIG. 11 shows results of the Kaplan-Meier method. The solid line shows results for the ketogenic diet non-administered group. The dotted line shoals the ketogenic diet administered group. The vertical axis indicates the survival rate, and the horizontal axis indicates the time (days) since joining the cohort. Log-rank test was used as the analytical method. The numerical value "No. at Risk" under the graph refers to the number of patients who can potentially die at each point in time, for patients with no ketogenic diet in the top row and for patients with ketogenic diet in the bottom row (the graph is described in this manner because final confirmed for case 4 was on day 894, such that case 4 would be missing).

Next, the survival rate for 5 cases in this Example was evaluated by the Kaplan-Meier method. Survival curves (3 years) were plotted for five lung cancer patients, i.e., two patients who did not undergo a ketogenic dietary therapy and three patients who did. Log-rank test was used as the analytical method. The curve confirms the effect of improvement in survival rate by ketogenic diet by the extension of survival period after therapy. Described under the graph is the number of live subjects who can potentially pass away by the presence/absence of ketogenic diet on day 0 (as of joining the cohort), day 200, day 400, day 600, day 800, day 1000, and day 1200. When tested whether the data is statistically significant, it was found that the survival period is significantly prolonged at $p<0.05$ (0.038). As a result, improvement in life prognosis was observed in the ketogenic diet administered group (FIG. 11). Thus, it was discovered that the dietary therapy of the invention has a significant effect.

Example 3

In this Example, DNA microarray analysis was conducted using RNA derived from peripheral blood mononuclear cells of non-small cell pulmonary malignant tumor patients.

(Method)

RNA was extracted from peripheral mononuclear cells of three patients (two CR patients and one PD patient) to whom ketogenic diet was introduced in Example 2. Total RNA before ketogenic diet therapy and after 1 year of ketogenic diet therapy was analyzed. RNA was extracted using QIAGEN RNeasy mini kit. Agilent Expression Array (SurePrint G3 Human Gene Expression 8×60K v3) was used to analyze gene expression. After normalizing the array data, differentially expressed genes were extracted.

(Calculation and Scaling of Signal Value)

Scaling was performed in accordance with the following procedure so that the mean values of signal values are the same between compared chips.

1) Removal of control gene group: select "0" in "ControlType".
2) Calculate trim signal mean value of probes excluding the top 2% and bottom 2% for a total of 4% of gProceedSignal
3) Calculation of scaling factor scaling factor=target signal constant (2500)/each array's trim signal mean value 4) Calculate a signal value by multiplying the scaling factor by individual probe signal value (gScale Signal)

(Filtering)

Data with low reliability were removed based on flags derived from Feature Extraction shown in Table 7.

TABLE 7

| Determination of effectiveness (SignalEvaluation) | | | | | | |
|---|---|---|---|---|---|---|
| Determination of effectiveness | Explanation | Feature Extraction derived flags | | | | |
| | | (1) | (2) | (3) | (4) | (5) |
| 2 | Transcription product was detected | 0 | 0 | 0 | 1 | 1 |
| 1 | Transcription product was detected, but judgment is difficult | one of them is "1" | | | 1 | 1 |
| | | | | | 1 | 0 |

TABLE 7-continued

Determination of effectiveness (SignalEvaluation)

| Determination of effectiveness | Explanation | Feature Extraction derived flags | | | | |
|---|---|---|---|---|---|---|
| | | (1) | (2) | (3) | (4) | (5) |
| 0 | Transcription product is not detected | | | | 0 | 0 |

*Considered feature extraction derived flags
(1) IsSaturated:saturation spot is displayed as "1"
(2) IsFeatNonUnifOL:if pixels of the spot are non-uniform, display "1"
(3) IsBGNonUnifOL:if pixels of background are non-uniform, display "1"
(4) IsPosAndsignif:if signal and background are not significantly different, display "0"
(5) IsWellAboveBG:if the sum of background signal strength and standard deviation is greater than signal value, display "0" (if BGSubSignal ≤ 13BGPixSDev: "0")

(Pattern Analysis)

After calculating the mean signal value of SET A for effective probes obtained by the aforementioned filtering, expression ratio relative to a control was calculated under the following condition for each SET:

Expression ratio=log2 (comparative group/control group).

The resulting expression ratio was used to extract a probe group showing expression ratio±2-fold or greater and expression difference (variation of signal value) of 100 or greater in one of the SETs.

To classify the extracted probes by each behavioral pattern after ketogenic diet therapy compared to before the therapy, the following threshold values were applied to define Up/Down/No change as follows.
2-fold or greater (for Log2 Ratio: 1) or greater: Up
½-fold or less (for Log2 Ratio: −1) or greater: Down
Others: No change Two patients (two CR patients) for whom ketogenic diet therapy resulted in complete response were categorized as set A, and one patient (one PD patient) for whom ketogenic diet had an effect but did not result in remission was categorized as set B. Comparative samples were classified into the following groups according to the definitions.

TABLE 8

| Group | A | B | Number of probes |
|---|---|---|---|
| 1 | Up | Up | 7 |
| 2 | Up | No change | 601 |
| 3 | Up | Down | 3 |
| 4 | No change | Up | 271 |
| 5 | No change | Down | 101 |
| 6 | Down | Up | 2 |
| 7 | Down | No change | 125 |
| 8 | Down | Down | 5 |

(Results)

After scaling and calculating a signal value, 32447 genes were excluded by filtering to extract 28454 genes. A group of 1115 probes exhibiting Ratio>=±2 and Differential>=100 were extracted to exclude 27339 genes. Differential of 2 fold or greater was defined as Up, ½ fold or less as Down, and others as No change. Two cases exhibiting CR were categorized as Set A, and the case exhibiting PD was categorized as Set B. Reaction patterns of each set was combined and classified into 8 groups. KEGG pathway frequency analysis detected groups of genes such as Group 1 (Set A Up/Set B Up) HIV-I infection p=0369, telomerase reverse transcriptase, Group 4 (Set A No change/Set B Up) Non-small cell lung cancer p=0.0121, PI3-kinase, Group 7 (Set A Down/Set B no change) NF-kappa B signaling pathway, p<0.0001, TNF-α, IL-1β, IL-8, and Group 8 (Set A Down/Set B Down) Nitrogen metabolism, p=0.0049, carbonic anhydrase I. Especially in Group 7 with a significant decrease in Set A but no change in Set B, inflammatory markers involved with an NFκB signaling pathway were classified.

(Discussion)

In group 4, CR cases showed no change, but for the PD case, PI3 kinase related to insulin signals was shown to be functioning, even when available carbohydrate was drastically reduced. This suggests that activation of an insulin signal that is non-dependent on insulin is involved in the growth of cancer. Importantly, while improvement in inflammation associated gene was not observed for the PD case, inflammation associated genes were improved in group of patients exhibiting complete response to ketogenic diet therapy in lung cancer patients as can be seen from Group 7. Thus, this suggests the possibility that an anti-inflammatory effect is exhibited with ketogenic diet therapy, which improves the pathology and exerts an anti-tumor effect. This result is consistent with the suppression of inflammatory cytokines in mice given a ketogenic formula in Example 1.

Example 4: Investigation with Other Patients: Example with Recurrent Breast Cancer It was studied whether therapy would succeed in patients with other cancer.

In this Example, recurrent breast cancer patients had practiced available carbohydrate restricted high fat diet of the invention for 3 months. The protocol was in accordance with Example 2.

This Example was carried out for only 3 months, but a significant decrease in tumor markers was observed by practicing the available carbohydrate restricted high fat diet of the invention from the early stages of the therapeutic period. The cases and results are shown in the following Table.

TABLE 9

| | | | | | | | | | |
|---|---|---|---|---|---|---|---|---|---|
| ↓Age as of date of consent | | | | | | | | | |
| Case number | Sex | Age | Height | Body weight | BMI | Disease | TNM classification | STAGE | Tissue |
| 6 | F | 69 | 156 | 47.1 | 19.4 | Right breast cancer post-operational recurrence | T4N3M1 | 4 (distant metastasis, 6th recurrence therapy) Phrenic lymph | Unknown |

TABLE 9-continued

↓Age as of date of consent

| Case number | Sex | Age | Height | Body weight | BMI | Disease | TNM classification | STAGE | Tissue |
|---|---|---|---|---|---|---|---|---|---|
| | | | | | | | | | node Local recurrent chest wall Hilar lymph node |

TABLE 10

| Case number | Previous chemotherapy | History of radiation therapy | History of surgery |
|---|---|---|---|
| 6 | UFT 400 mg/day Norvadex May 1995 to April 2000 Furtulon 600 mg/day September 1998 TAM discontinued Fareston 400 mg/day | Right armpit, above collarbone 50 Gy August to September 1991 Right chest wall 40 Gy July to August 1995 Phrenic lymph node metastasis 60 Gy July to August 2014 | Mamma resection/armpit lymph node dissection July 1991 Right chest wall skin resection April 1995 |

The following results were obtained. Data is similar to FIGS. 7 to 10. Data for 3 tumor markers are also included. In the Table, W indicates weeks and M indicates months.

TABLE 11

| Venous blood acetoacetic acid (μmol/L) | | | | Venous blood β-H butyric acid (μmol/L) | | | | CEA (ng/ml) | | | | CA15-3 (U/mL) | | | | NCC-ST-439 (U/ml) | | | |
|---|---|---|---|---|---|---|---|---|---|---|---|---|---|---|---|---|---|---|---|
| Before | 1 W | 1 M | 3 M | Before | 1 W | 1 M | 3 M | Before | 1 M | 2 M | 3 M | Before | 1 M | 2 M | 3 M | Before | 1 M | 2 M | 3 M |
| 70 | 1012 | 284 | 285 | 125 | 2318 | 538 | 672 | 5 | 4 | 4 | 4 | 155.3 | 124.2 | 117.4 | 129.3 | 150 | 73 | 56 | 48 |

CEA, CA15-3, and NCC-ST-439 in Table 11 are tumor markers. Surprisingly, a significant decrease in tumor markers was observed, and observation found cancer to be improving by only practicing an early stage (introductory stage) therapy. Considering that there was hardly any effect up to a fifth time in a patient with a sixth recurrence, judgment from tumor markers suggest that the dietary therapy of the invention has succeeded regardless of other anticancer therapy, suggesting that introduction of dietary therapy alone can be successful when the results in Examples 2 are taken into consideration therewith. Further, the prognosis during the introductory stage is already showing improvement, which suggests that treatment (dietary therapy) during the introductory stage alone would also succeed. In these cases, blood glucose, insulin, 1,5-AG, HbA1c, T-cho, TG, HDL-c, LDL-c, UA, and CRP were not particularly problematic.

Example 5: Investigation of Other Cases

In this Example, available carbohydrate restricted high fat diet similar to that in Example 2 was practiced by cancer patients other than those in Examples 2 and 4 (case 8, case 11, and case 12). Endpoints were recorded and evaluated in the same manner as Example 2. Table 12 shows information for each case.

TABLE 12

| Case | Carcinoma | Sex | Age | Other | 3 M | 12 M | Alive | Numbers of days of survival | Continuation | Therapeutic effect |
|---|---|---|---|---|---|---|---|---|---|---|
| 7 | Pulmonary adenocarcinoma (stage IV) | M | 67 | Withdrew consent | | | | | | |
| 8 | Uterine body cancer (stage IV B) | F | 65 | | ○ | × | × | 111 | × | PD |

TABLE 12-continued

| Case | Carcinoma | Sex | Age | Other | 3 M | 12 M | Alive | Numbers of days of survival | Continuation | Therapeutic effect |
|---|---|---|---|---|---|---|---|---|---|---|
| 9 | Bladder cancer (stage IV) | F | 51 | Dicontinued for other reasons | × | × | × | 130 | × | |
| 10 | Pulmonary adenocarcinoma (stage IV) small cell cancer | M | 62 | Left | | | | | | |
| 11 | Right ovarian cancer re-recurrence | F | 56 | Completely healed and resected Currently still ongoing | ○ | | ○ | 337 | ○ | CR |
| 12 | Peritoneal cancer | F | 50 | | ○ | | ○ | 288 | ○ | PR |

*Number of days survival from date of IC as of Sep. 1, 2016

Cases 7 and 10 are examples that did not reach ketogenic diet introduction, with poor prognosis. Case 9 is also an example that did not reach ketogenic diet introduction, passing away in 130 days from the date of IC.

Each case is disclosed in detail below.

(Case 8)

Case: 65 years old female, diagnosis of uterine body cancer (stage IIIa)

(Therapeutic Progress)

July 2014: hysterectomy+both uterine appendage excision+pelvis lymph node dissection+paraaortic lymph node dissection+Douglas' pouch peritoneum detachment surgery were performed.

4 courses of chemotherapy (TAC therapy) were carried out post-surgery.

T=docetaxel (Taxotere)

A=doxorubicin hydrochloride (Adriamycin)

C=cyclophosphamide

December 2014: 6 courses of chemotherapy were completed.

March 2015: autologous cancer vaccine was scheduled three times in two weeks.

March to July 2015: Retronectin-induced T cell therapy was administered once every two weeks.

September 2015: ketogenic diet introduction was started.

(Case 11)

Case: 56 years old female diagnosis of ovarian cancer (stage IIc)

(Therapeutic Progress)

October 2003: the patient was diagnosed with ovarian cancer (stage IIc).

November 2003: simple hysterectomy+both uterine appendage excision+pelvis lymph node dissection and paraaortic lymph node dissection+pan-omentectomy+appendectomy were performed.

November 2011: ovarian cancer recurred

December 2011: abdominal tumorectomy+lower anterior resection+partial resection of small bowel were performed.

January to August 2011: 6 courses of TC therapy were administered.

September 2015: the patient was diagnosed with re-recurrence of ovarian cancer.

October 2015: TC therapy was started.

November 2015: introduction of ketogenic diet was started.

April 2016: tumorectomy+lower anterior resection+DJ catheterization were performed, and cancer was completely resected; ketogenic diet is still ongoing.

(Case 12)

Case: 50 years old female diagnosis of peritoneal cancer (stage IIIa)

(Therapeutic Progress)

January 2011: the patient was diagnosed with peritoneal cancer (stage IIIa), and 6 courses of TC were administered from February to August 2011.

July 2012: liver metastasis to liver S7 was found, and 6 courses of TC were administered.

August 2014: liver metastasis and multiple lymph nodes recurrence were found, and 7 courses of Doxil+CBCDA were administered.

July 2015: re-recurrence was found.

November 2015: introduction of ketogenic diet was started.

(Results)

Table 13 shows data for blood ketone body, glycometabolism, lipid, QOL, gastrointestinal symptom, and tumor marker of case 8. FIG. 13 shows CT images of case 8 before and after introduction of ketogenic diet. Table 14 shows data for blood ketone body, glycometabolism, lipid, QOL, GSRS, and tumor marker of case 11. FIGS. 14 to 16 show PET-CT images of case 11 before and after introduction of ketogenic diet. Table 15 shows data for blood ketone body, glycometabolism, lipid, QOL, GSRS, and tumor marker of case 12. FIGS. 17 to 19 show PET-CT images of case 12 before and after introduction of ketogenic diet.

TABLE 13

| | | | | | Case 8 | | | |
|---|---|---|---|---|---|---|---|---|
| Evaluation index | | Before | 3 w | 2 m | 3 m | | | |
| Blood ketone body | Venous blood acetoacetic acid (μmol/L) | 809 | 1868 | 1390 | 1510 | | | |
| | Venous blood β-H butyrate (μmol/L) | 1827 | 4038 | 3284 | 6385 | | | |
| | Uric acid (mg/dL) | 4.1 | 8.3 | 8.7 | 9.3 | | | |
| | CRP (mg/dL) | 5.96 | 7.00 | 5.13 | 2.78 | | | |
| Blood data Glyco-metabolism | Glucose (mg/dL) | 110 | 104 | 106 | 111 | | | |
| | Insulin (μU/mL) | 2.7 | 3.2 | 0.9 | 1.2 | | | |
| | 1,5-AG (μmol/mL) | 5.0 | | | | | | |
| | HbA1c (NGSP) (%) | 6.2 | | | 5.7 | | | |
| Blood data Lipid | T-Cho (mg/dL) | 219 | 208 | 227 | 296 | | | |
| | TG (mg/dL) | 127 | 151 | 145 | 258 | | | |
| | HDL-C (mg/dL) | 46 | 46 | 61 | 59 | | | |
| | LDL-C (mg/dL) | 134 | 125 | 123 | 175 | | | |

| Evaluation index | | Before | 1 m | 2 m | | | | |
|---|---|---|---|---|---|---|---|---|
| EORTC QLQ-C30 | Systemic condition scale | 33.3 | 75.0 | 83.3 | | | | |
| | Function scale, emotion | 83.3 | 100.0 | 91.7 | | | | |
| | Symptom scale, fatigue | 55.6 | 33.3 | 33.3 | | | | |
| | Symptom scale, insomnia | 33.3 | 33.3 | 33.3 | | | | |
| GSRS | GSRS score | 3.2 | 2.1 | 2.1 | | | | |
| | Acid reflux | 5.0 | 3.5 | 3.0 | | | | |
| | Indigestion | 2.8 | 2.0 | 1.8 | | | | |
| | Constipation | 3.7 | 2.3 | 2.3 | | | | |
| Tumor marker | CA19-9 (U/mL) | Aug. 24, 2015 | Sep. 16, 2015 | Sep. 25, 2015 | Oct. 7, 2015 | Nov. 4, 2015 | Dec. 16, 2015 | |
| | | 33 | 48 | | 51 | 84 | 163 | |
| | CA125 (U/mL) | Apr. 15 2015 | Jun. 24, 2015 | Jul. 22, 2015 | Aug. 24, 2015 | Sep. 25, 2015 | Oct. 7, 2015 | Nov. 4, 2015 | Dec. 16, 2015 |
| | | 12 | 431 | 2107 | 6815 | 5413 | 4486 | 6608 | 7483 |
| | CEA (ng/mL) | Aug 24, 2015 | Sep. 16, 2015 | Sep. 25, 2015 | Oct. 7, 2015 | Nov. 4, 2015 | Dec. 16, 2015 | |
| | | <1 | 1 | | 2 | 2 | 3 | | |

TABLE 14

| Case 11 | Evaluation index | | Before | 1 m | 2 m | 3 m | 6 m |
|---|---|---|---|---|---|---|---|
| | Blood ketone body | Venous blood acetoacetic acid (μmol/L) | 25 | 218 | 231 | 218 | 369 |
| | | Venous blood β-H butyrate (μmol/L) | 30 | 739 | 753 | 588 | 813 |
| | | Uric acid (mg/dL) | 2.4 | 2.3 | 3.4 | 2.7 | 4.0 |

TABLE 14-continued

| | | | | | | |
|---|---|---|---|---|---|---|
| | CRP (mg/dL) | 0.04 | 0.04 | 0.04 | 0.04 | 0.14 |
| Blood data Glycometabolism | Glucose (mg/dL) | 128 | 106 | 104 | 101 | 110 |
| | Insulin (μU/mL) | 37.4 | 8.1 | 6.0 | 5.7 | 23.1 |
| | 1,5-AG (μmol/mL) | 1.7 | 1.1 | 1.1 | 1.2 | 1.7 |
| | HbA1c (NGSP) (%) | 5.8 | 5.7 | 4.6 | 5.0 | 5.1 |
| Blood data Lipid | T-Cho (mg/dL) | 129 | 177 | 198 | 162 | 204 |
| | TG (mg/dL) | 90 | 40 | 43 | 37 | 94 |
| | HDL-C (mg/dL) | 49 | 59 | 67 | 58 | 62 |
| | LDL-C (mg/dL) | 59 | 95 | 104 | 81 | 113 |
| EORTC QLQC30 | Systemic condition scale | 33.3 | 75.0 | 100.0 | 83.3 | 50.0 |
| | Function scale, emotion | 58.3 | 83.3 | 100.0 | 100.0 | 91.7 |
| | Symptom scale, fatigue | 66.7 | 44.4 | 0.0 | 0.0 | 66.7 |
| | Symptom scale, insomnia | 33.3 | 33.3 | 0.0 | 0.0 | 0.0 |
| GSRS | GSRS score | 1.8 | 1.3 | 1.0 | 1.1 | 1.2 |
| | Acid reflux | 1.0 | 1.0 | 1.0 | 1.0 | 1.0 |
| | Indigestion | 2.0 | 1.0 | 1.0 | 1.0 | 1.0 |
| | Constipation | 2.7 | 1.7 | 1.0 | 1.0 | 1.7 |

| Evaluation index | | Jun. 11, 2015 | Sep. 14, 2015 | Oct. 2, 2015 | Oct. 21, 2015 | Nov. 4, 2015 | Dec. 2, 2015 |
|---|---|---|---|---|---|---|---|
| Tumor marker | CA19-9 (U/mL) | 10 | 60 | 70 | 28 | 10 | 13 |
| | CA125 (U/mL) | 19 | 45 | 55 | 19 | 11 | 12 |
| | CEA (ng/mL) | <1 | 1 | <1 | 1 | 1 | 1 |

| Evaluation index | | Jan. 6, 2016 | Feb. 3, 2016 | Mar. 2, 2016 | May 18, 2016 | Jun. 15, 2016 |
|---|---|---|---|---|---|---|
| Tumor marker | CA19-9 (U/mL) | 4 | 5 | 8 | 4 | 3 |
| | CA125 (U/mL) | 10 | 11 | 13 | 13 | 13 |
| | CEA (ng/mL) | 1 | 2 | 1 | 1 | <1 |

TABLE 15

Case 12

| Evaluation index | | Before | 1 m | 2 m | 3 m |
|---|---|---|---|---|---|
| Blood ketone body | Venous blood acetoacetic acid (μmol/L) | 27 | 459 | 510 | 293 |
| | Venous blood β-H butyrate (μmol/L) | 56 | 1167 | 1031 | 538 |
| | Uric acid (mg/dL) | 5.8 | 5.1 | 3.3 | 3.0 |
| | CRP (mg/dL) | 1.19 | 2.17 | 0.30 | 3.44 |
| Blood data Glycometabolism | Glucose (mg/dL) | 101 | 108 | 99 | 98 |
| | Insulin (μU/mL) | 9.8 | 7.1 | 7.8 | 3.6 |
| | 1,5-AG (μmol/mL) | 27.7 | 20.1 | 10.4 | 6.8 |
| | HbA1c (NGSP) (%) | 5.5 | 5.9 | 5.4 | 5.3 |
| Blood data | T-Cho (mg/dL) | 260 | 275 | 363 | 279 |

TABLE 15-continued

| | | Case 12 | | | |
|---|---|---|---|---|---|
| Lipid | TG (mg/dL) | 134 | 163 | 141 | 67 |
| | HDL-C (mg/dL) | 43 | 46 | 74 | 61 |
| | LDL-C (mg/dL) | 177 | 195 | 245 | 194 |
| EORTC QLQC30 | Systemic condition scale | 41.7 | 16.7 | 66.7 | 66.7 |
| | Function scale, emotion | 41.7 | 33.3 | 75.0 | 75.0 |
| | Symptom scale, fatigue | 44.4 | 66.7 | 33.3 | 33.3 |
| | Symptom scale, insomnia | 33.3 | 33.3 | 33.3 | 66.7 |
| GSRS | GSRS score | 1.5 | 2.0 | 1.3 | 1.1 |
| | Acid reflux | 1.0 | 2.0 | 1.0 | 1.0 |
| | Indigestion | 1.5 | 1.5 | 1.0 | 1.0 |
| | Constipation | 2.3 | 3.0 | 2.0 | 1.3 |

| Evaluation index | | Nov. 4, 2015 | Dec. 16, 2015 | Jan. 13, 2016 | Feb. 10, 2016 |
|---|---|---|---|---|---|
| Tumor marker | CA19-9 (U/mL) | 25 | 28 | 28 | 30 |
| | CA125 (U/mL) | 109 | 41 | 27 | 27 |
| | NSE (ng/mL) | 15.0 | 17.7 | 16.5 | 15.6 |
| | CEA (ng/mL) | 2 | 2 | 1 | 1 |
| | CYFRA (ng/mL) | 4.4 | 1.8 | 1.5 | 1.8 |

The disease background was two patients with lung cancer, one patient with recurrence of uterine body cancer, one patient with recurrence of bladder cancer, one patient with second recurrence of ovarian cancer, and one patient with a fourth recurrence of peritoneal cancer. Of the two lung cancer patients, one had nausea and the other had a transformation from adenocarcinoma into small cell cancer, so that the test was discontinued. Therapy for one patient with bladder cancer was discontinued due to an adverse event involving another cancer therapy. In the discontinued bladder cancer case, the subject passed away immediately thereafter. Patients of two discontinued lung cancer cases also had extremely unfavorable prognosis. These no treatment group can be evaluated as comparative examples. Cases that can be evaluated as Examples were 3 cases. Blood ketone bodies exhibited an increasing trend in acetoacetic acid and β-H butyrate in one month. Hypoglycemia, nausea, fatigue or the like was not observed, and GSRS score showed an improving trend in 3 months. Systemic condition scale slightly worsened. PET-CT after 3 months showed SD (=stable disease) in the uterine body cancer case, and PR (=partial response) in the ovarian cancer and peritoneal cancer cases. One uterine body cancer patient had strong ascites upon introduction. However, after supplementing nutrition with mainly ketogenic formula, ascites improved from CA125 6815→4486 U/ml one month after the introduction of ketogenic diet, despite rapid exacerbation prior to the introduction of ketogenic diet. Improvement in tense ascites and decrease in pleural effusion were also observed (FIG. 13), and QOL also improved, e.g., the patient was allowed to leave the hospital, but resumption of chemotherapy was denied and the patient passed away after 4 months from the introduction. However, this uterine body cancer patient case can be medically evaluated as showing a significant effect compared to cases without practicing the present invention. Currently as of July 2016, the other two patients are alive. For the ovarian cancer case, complete cure surgery has been performed and cancer is currently in remission. Of the three patients, two ovarian cancer and peritoneal cancer patients exhibited PR by introduction of ketogenic diet. Thus, ketogenic diet therapy was also safely practiced in patients with cancer other than lung cancer and breast cancer, which suggests the potential of exerting a life-prolonging effect. In cases that did not reach the introduction of ketogenic diet (two lung cancer patients and one patient with recurrence of bladder cancer), an improvement observed in cases with introduction of ketogenic diet was not found.

In case 8, tense ascites and pleural effusion on the back side were found prior to the introduction of ketogenic diet, but tense ascites was improved and pleural effusion decreased after the introduction of ketogenic diet (FIG. 13). For case 11, it can be determined from the radiological interpretation that the lump on the left side of the pelvis seen in PET before the introduction of ketogenic diet has contracted, especially in the cyst portion, and FDG accumulation was also alleviated (SUVMax prior to introduction of ketogenic diet 15.7→after introduction of ketogenic diet 10.2). The lump on the head side of the portion of the operated sigmoid colon was also in a contracting trend, and FDG accumulation was also in an alleviating trend (SUVMax 14.9→11.4). Further, metastasis or abnormal accumulation that would suggest recurrence was not found. In this manner, case 11 exhibited an improving trend from PET observation (FIGS. 14 to 16). For case 12, it is determined from radiological interpretation that the accumulation at the right pleura has decreased (SUVMax 7.9→4.1), and the shades of nodes at the right interloper pleura has contracted. It was suspected that the activity of pleural dissemination after the introduction of ketogenic diet decreased. Furthermore, pleural effusion was found to be reduced after the introduction of ketogenic diet compared to before the introduction of ketogenic diet (FIGS. 18 and 19).

Table 16 shows the results of evaluation indices of blood ketone bodies, QOL, and tumor markers of two patients exhibiting CR and PR by ketogenic diet introduction. As shown, it is understood that the ketone body count increases significantly, and tumor markers are significantly improved or the increase thereof is suppressed.

TABLE 16

| | | Case 11 | | | | |
|---|---|---|---|---|---|---|
| Evaluation index | | Before | 1 M | 2 M | 3 M | 6 M |
| Acetoacetic acid | | 25 | 218 | 231 | 218 | 369 |
| β-H butyrate | | 30 | 739 | 753 | 588 | 813 |
| Glucose | | 128 | 106 | 104 | 101 | 110 |
| EORTC QLQ-C30 | Systemic condition scale | 33.3 | 75.0 | 100.0 | 63.3 | 50.0 |
| | Fatigue | 66.7 | 44.4 | 0.0 | 0.0 | 66.7 |
| GSRS | | 1.8 | 1.3 | 1.0 | 1.1 | 1.2 |

TABLE 16-continued

Case 12

| Evaluation index | | Before | 1M | 2M | 3M |
|---|---|---|---|---|---|
| Acetoacetic acid | | 27 | 459 | 510 | 293 |
| β-H butyrate | | 56 | 1167 | 1031 | 538 |
| Glucose | | 101 | 108 | 99 | 98 |
| EORTC QLQ-C30 | Systemic condition scale | 41.7 | 16.7 | 66.7 | 66.7 |
| | Fatigue | 44.4 | 66.7 | 33.3 | 33.3 |
| GSRS | | 1.5 | 2.0 | 1.3 | 1.1 |
| Tumor marker | CA19-9 | 25 | 28 | 28 | 30 |
| | CA125 | 109 | 41 | 27 | 27 |
| | NSE | 15.0 | 17.7 | 16.5 | 15.6 |
| | CEA | 2 | 2 | 1 | 1 |
| | CYFRA | 4.4 | 1.8 | 1.5 | 1.8 |

Example 6

Ketogenic diet was also introduced into the following patients. Excellent results are about to be achieved.

Case 13: rectal cancer, multiple liver metastasis, female, 29 years old, number of days of survival: 199 days Case 14: post-operation recurrence of bladder cancer, male, 71 years old, number of days of survival: 80 days Case 15: labial gland-like cystic cancer, bone metastasis, male, 46 years old, number of days of survival: 71 days (number of days of survival from the date of IC is as of Sep. 1, 2016)

The present invention was explained above based on the Examples. The Examples are only exemplification. It is understood by those skilled in the art that various modified examples are possible, and such modified examples are also within the scope of the present invention.

As described above, the present invention is exemplified by the use of its preferred embodiments. However, it is understood that the scope of the present invention should be interpreted solely based on the Claims. It is also understood that any patent, any patent application, and any references cited herein should be incorporated herein by reference in the same manner as the contents are specifically described herein. The present application claims priority to Japanese Patent Application No. 2015-175198 filed on Sep. 4, 2015 in Japan. The entire content of these applications is incorporated herein by reference.

INDUSTRIAL APPLICABILITY

The present invention provides usefulness to the field of cancer therapy and the dietary therapy industry.

The invention claimed is:

1. A method for treating cancer in a subject, comprising feeding the subject a composition comprising high fat diet or a combination of compositions comprising high fat diet, wherein fat in the high fat diet is about 120 g or greater per day based on a real body weight of 50 kg, and wherein the high fat diet restricts carbohydrate to less than 30 g per day.

2. The method according to claim 1, wherein daily caloric intake in the high fat diet is 20 kcal/kg body weight or greater.

3. The method of claim 1, wherein the cancer is a colon tumor.

4. The method of claim 1, wherein the cancer is selected from pulmonary adenocarcinoma, non-small cell lung cancer, uterine cancer, bladder cancer, ovarian cancer, peritoneal cancer, and breast cancer.

5. The method of claim 1, wherein the cancer is selected from uterine cancer, bladder cancer, peritoneal cancer, and breast cancer.

* * * * *